United States Patent [19]

Kopf

[11] Patent Number: 5,593,580

[45] Date of Patent: Jan. 14, 1997

[54] FILTRATION CASSETTE ARTICLE, AND FILTER COMPRISING SAME

[76] Inventor: Henry B. Kopf, 108 Coatbridge Cir., Cary, N.C. 27511

[21] Appl. No.: 405,493

[22] Filed: Mar. 15, 1995

Related U.S. Application Data

[63] Continuation-in-part of Ser. No. 19,362, Mar. 1, 1994, Pat. No. Des. 357,059, Ser. No. 442,240, Nov. 28, 1989, Pat. No. 5,528,713, and Ser. No. 207,655, Jun. 21, 1988, said Ser. No. 442,240, is a division of Ser. No. 936,486, Nov. 26, 1986, Pat. No. 4,885,087.

[51] Int. Cl.⁶ ............................................. B01D 63/00
[52] U.S. Cl. ............................. 210/321.75; 210/321.84; 210/488; 210/489; 210/231; 210/232; 210/456
[58] Field of Search .................... 210/321.72, 321.75, 210/321.84, 489, 231, 232, 228, 323.1, 227, 488, 456

[56] References Cited

U.S. PATENT DOCUMENTS

| Des. 324,720 | 3/1992 | Kopf | D23/209 |
|---|---|---|---|
| Des. 327,313 | 6/1992 | Kopf | D23/209 |
| 744,761 | 11/1903 | James . | |
| 802,105 | 10/1905 | Johnson, et al. . | |
| 1,138,251 | 5/1915 | Schaefer . | |
| 1,282,414 | 12/1918 | Hagstrom . | |
| 1,540,251 | 9/1925 | Buckley et al. . | |
| 2,390,628 | 12/1945 | Van Winkle | 210/188 |
| 2,473,986 | 9/1949 | Booth | 210/185 |
| 2,590,242 | 3/1952 | Fusco | 210/188 |
| 3,221,883 | 12/1965 | Linnstrom | 210/228 |
| 3,520,803 | 7/1970 | Iaconelli . | |
| 3,585,131 | 6/1971 | Esmond . | |
| 3,988,242 | 10/1976 | Kurita et al. | 210/227 |
| 4,229,304 | 10/1980 | Fismer | 210/231 |
| 4,235,721 | 11/1980 | Nakamura et al. | 210/227 |
| 4,310,416 | 1/1982 | Tanaka et al. . | |
| 4,411,784 | 10/1983 | Esmond . | |
| 4,430,218 | 2/1984 | Perl et al. . | |
| 4,540,492 | 9/1985 | Kessler | 216/651 |
| 4,543,187 | 9/1985 | Stepacher | 210/232 |
| 4,624,784 | 11/1986 | Lefebvre . | |
| 4,735,718 | 5/1986 | Peters . | |
| 4,750,983 | 6/1988 | Foster et al. | 204/301 |
| 4,769,140 | 9/1988 | Van Dijk et al. | 210/184 |

(List continued on next page.)

FOREIGN PATENT DOCUMENTS

| 36926 | 8/1984 | European Pat. Off. . |
|---|---|---|
| 2930986 | 2/1980 | Germany . |
| 229603 | 1/1985 | Germany . |
| 1392030 | 4/1975 | United Kingdom . |
| 8600237 | 1/1986 | WIPO . |

OTHER PUBLICATIONS

Prostak™ Bench Top Development System Lit. No. SD200 Aug. 1988.
"Laboratory Ultrafiltration Products for Improved Biologicals Recover" Lit. No. AB841, Oct. 1988.
"Shoten the Race to the Market with Millipore Pilot and Process Systems." Lit. No. SD100 Jan. 1988.
Minisette$^R$ Systems, Tangential Ultrafiltration and Microfiltration Membrane Cassette Systems for Processing Volumes of 1–20 Liter Batches. Product Brochure of Filtron Technology Corporation, 50 Bearfoot Road, Northborough, MA 01532, Copr. 1989, Literature No. FPL004.
Microporous Filters, OHV Configuration Installation Instructions, Copr. 1978, Millipore Corporation, Bedford, MA, Product Literature Part No. 6847.

*Primary Examiner*—Ana Fortuna
*Attorney, Agent, or Firm*—Steven J. Hultquist

[57] ABSTRACT

A filtration cassette, of a type comprising membrane filter sheets arranged in a peripherally bonded array of multilaminate character wherein the filter sheets alternate with foraminous (e.g., screen or mesh) sheet members, ribbed retentate sheet members, and a cross-flow filter comprising a multiplicity of stacked filtration cassettes of such type. The filtration cassettes and filter of the invention may be advantageously employed for dewatering of aqueous biomass suspensions, desalting of proteins, removal of secreted metabolites from cellular suspensions, and the like.

29 Claims, 13 Drawing Sheets

U.S. PATENT DOCUMENTS

| | | | |
|---|---|---|---|
| 4,801,381 | 1/1989 | Niesen | 210/321.84 |
| 4,867,876 | 9/1989 | Kopf | 210/228 |
| 4,885,087 | 12/1989 | Kopf | 210/321.72 |
| 5,049,268 | 9/1991 | Kopf . | |
| 5,232,589 | 8/1993 | Kopf | 210/321.75 |
| 5,342,517 | 8/1994 | Kopf | 210/228 |
| 5,437,796 | 8/1995 | Brüschke et al. | 210/321.75 |
| 5,445,737 | 8/1995 | Ondrick | 210/321.75 |

# 5,593,580

FILTRATION CASSETTE ARTICLE, AND FILTER COMPRISING SAME

CROSS-REFERENCE TO RELATED APPLICATIONS

This is a continuation in part of each of: (i) U.S. application Ser. No. 29/019,362 filed Mar. 1, 1994, now U.S. Pat. No. D357,059, (ii) U.S. application Ser. No. 07/442,240 filed Nov. 28, 1989 now U.S. Pat. No. 5,528,713, as a division of U.S. application Ser. No. 06/936,486 filed Nov. 26, 1989, now U.S. Pat. No. 4,885,087, and (iii) U.S. application Ser. No. 07/207,655 filed Jun. 21, 1988 pending.

BACKGROUND OF THE INVENTION

1. Field of the Invention

This invention relates generally to filtration cassettes, of a type comprising membrane filter sheets arranged in a multilaminate, peripherally bonded array wherein the filter sheets alternate with foraminous (e.g., screen or mesh) permeate sheet elements, and ribbed retentate channel elements. The invention further relates generally to cross-flow filters comprising a multiplicity of stacked filtration cassettes of such type, as well as to a method of making such filtration cassettes.

2. Description of the Related Art

Stacked plate cross-flow filters are utilized in a variety of solids-liquid separation operations, including the dewatering of solids-liquid suspensions such as aqueous biomass suspensions, the desalting of proteins, and the removal of secreted metabolites from cellular cultures.

In such systems, the stacked plates making up the cross-flow filter are typically mounted in a unitary frame structure whereby the respective plates are retained in alignment with one another, in a so-called "plate and frame" construction.

The plate and frame filter typically utilizes a unitary liquid feed conduit provided with openings at spaced intervals along its length and extending through the stacked plates as a means to introduce influent solids-containing liquid into the flow channels defined between adjacent plates in the stacked plate assembly. The flow channels in the plate and frame filter contain filter elements, such as disposable filter paper sheets or polymeric membranes, with which the solids-containing liquid is contacted and through which solids-depleted liquid passes. A unitary liquid withdrawal conduit featuring openings at spaced intervals along its length correspondingly extends through the stacked plates, in liquid flow communication with the respective flow channels of the stacked plate assembly, and conveys solids-depleted liquid out of the filter system.

As filtration proceeds, the filtered solids build up in the flow channels of the filter, on the "feed liquid sides", i.e., active filtration surfaces, of the filter sheets. The filter then is periodically backwashed, or alternatively, it may be fully shut down after a predetermined time or after a predetermined level of solids has accumulated in the flow channels on the filtration surfaces of the filter sheet elements, following which the system is drained of liquid, and the filter sheets replaced as necessary.

In one type of presently marketed stacked filter system, commercially available from Millipore Corporation (Bedford, Mass.) as the Prostak® cross-flow filter, the adjacent filter plates define a flow channel. Solids-containing influent liquid is fed at one side of the plate from a central location into a transversely extending feed distribution conduit, which is provided with openings at spaced-apart intervals along the length of the conduit for egress of the solids-containing liquid. At the opposite side of the adjacent plates, the flow channel is similarly constructed with a liquid collection conduit having openings along its length to collect the solids-depleted liquid and discharge same from a central outlet communicating with the collection conduit.

A major problem which has been encountered in cross-flow filters of the above-described type is that the liquid flow distribution, as for example reflected by the volumetric liquid flow rate or the liquid superficial velocity, is highly nonuniform in the transverse direction of the flow channel. Such maldistribution of the solids-containing liquid is a result of the fact that (1) the influent liquid is introduced into the feed distribution conduit at a central location, and (2) the cross sectional area of the liquid inlet is smaller than the sum of the inlet cross sectional areas of the cross flow subchannels.

Due to the pressure drop in the transverse direction, from the medial inlet port of filter plate assembly to the extremities of the feed distribution conduit, the local longitudinal flow (cross-flow) of liquid from the inlet side to the outlet side of the stacked plates, at progressively farther transverse distances from the central liquid inlet port, is progressively reduced in correspondence to the pressure drop experienced as the liquid is directed transversely to the outer extremities of the distribution conduit.

As a result, there is preferential channeling of the liquid at the central part of the flow channel from the inlet side to the outlet side thereof, and concomitant under-utilization of the peripheral areas of the filter. The available filter surface therefore is partially utilized in cross flow and partially in dead end filtration. When the solids in the central portion have been built up to a point requiring backwashing or cleaning of the filter, only that portion of the filter utilized in cross flow can be cleaned. The peripheral areas of the filter sheet remain fouled and cause carry-over of fouled material from one batch process to the next.

Such transverse maldistribution of the feed liquid in cross-flow filters of the aforementioned type could conceivably be overcome by the provision of header manifolds to introduce feed liquid into the filtration channels at multiple introduction points along the sides of the stacked filter plates, with a corresponding outlet header manifold arrangement at the opposite side of the stacked plates. Unfortunately, however, such provision would significantly increase the overall system pressure drop as well as the complexity of the filter system, since it would be necessary to positively seat the multiplicity of feed liquid branch lines passing from the manifold into the filter.

Another type of stacked plate cross-flow filter which has been commercialized employs a transversely extending liquid distribution conduit with spaced-apart openings therein to introduce solids-containing liquid into the flow channel between adjacent stacked plates, but instead of a central inlet port to flow the solids-containing liquid to such conduit, the liquid is axially fed into the conduit from a feed line connected to a transverse extremity of the conduit. Filters of such type are available from Millipore Corporation (Bedford, Mass.) under the trademark Pellicon®. This feed arrangement results in a progressive diminution of the liquid pressure at increasing transverse distances in the feed end of the distribution conduit, which in turn results in progressively transversely decreased cross-flow rates of liquid in the flow channel.

In an effort to overcome the aforementioned liquid flow maldistribution characteristics of stacked plate filters, filter plates have been constructed with baffle elements defining discrete flow channels, with the intent of achieving a more uniform distribution of the solids-containing influent liquid across the full areal extent of the filter elements in the flow channels of the filter.

A filter plate commercially available from Toyo Soda Manufacturing Company, Ltd. (Tokyo, Japan) has a structure in which solids-containing influent liquid is introduced to the flow channel at a central inlet port along side of the plate. A wall is disposed in front of the liquid inlet, extending upwardly from the floor of the flow channel and transversely toward the extremities of the flow channel, to divide the influent system into two outwardly directed streams. Downstream from such stream-splitting wall is a longitudinally extending divider partition, the steam-splitting wall and the divider partition together forming a "T" construction when viewed in plan view. Longitudinally spaced from a parallel to the stream-splitting wall are a series of baffle partitions on either side of the divider partition. The baffles extend transversely part-way across the flow channel on either side of the divider partition, so that there is formed a serpentine flow path for each of the split streams, on the respective sides of the partition. A unitary liquid outlet port is provided at the opposite side of the stacked plates from the inlet port, whereby the respective serpentine flows are finally joined and discharged from the flow channels of the filter.

Although the dual serpentine flow path arrangement described above provides a somewhat better distribution of liquid flow across the area extent of the filter paper element, the sharp turns in the flow path at the extremities of the baffles create edge and entrance effects in the flow streams which produce substantial dead space and bypassing therein. As a result of such anomalous flow phenomena, the filtration efficiency of the baffled serpentine flow arrangement is significantly reduced.

A microporous filter article is commercially available from Millipore Corporation (Bedford, Mass.) under the trademark MF-Millipore, as a stacked array comprising a top gasket sheet member, a filtrate separator plate, a filter sheet of microporous filtration medium, a retentate separator plate, a second filter sheet of microporous filtration medium, a filtrate separator plate, and a bottom gasket sheet member. The filtrate separator plates and the retentate separator plate include a peripheral border including manifold openings therein, circumscribingly enclosing a central screen or mesh flow channel area. In operation, a recirculating fluid path across the filter sheets is directed by the retentate screen, in the flow channel area of the retentate separator plate, which contacts the two filter sheets. The filter sheets separate the solution or other feed material to be separated, according to the porosity rating of the filter sheets. The filtrate screen, in the flow channel area of the filtrate separator plate, carries away the filtrate to the manifold openings in the peripheral borders of the filtrate separator plates. The filtrate then flows through the manifold openings of the filtrate separator plates to a filtrate collection means such as a vessel which is provided exteriorly of the filter comprising the stacked array of such filter articles.

Tangential ultrafiltration and microfiltration membrane cassette systems are available from Filtron Technology Corporation (Northborough, Mass.) under the trademarks Minisette, Centrasette, and Maxisette, which comprise multiple layers of membrane assemblies composed of ultra filtration or microfiltration membranes disposed between polymeric screen or linear open channel retentate separators and screen filtrate separators. Blocked borders on the filtrate and retentate screens direct the filtrate to collection ports on a bottom cell manifold. Cassettes can be provided in a stacked array, or cell, mounted between end plates, which may be provided with suitable ports, for introduction of feed material to be separated in the cassettes, and for discharge or withdrawal of filtrate and retentate.

My prior U.S. Pat. No. 4,882,050 issued Sep. 19, 1989 describes a filter plate characterized by substantially uniform transverse distribution of liquid from a unitary liquid feed port, and highly uniform liquid cross-flow across the full transverse extent of the flow channel formed when plates of such type are stacked to form a cross-flow filter.

The filter plate of this prior patent has a generally planar and rectangular shape with a substantially flat bottom surface. A top surface of the plate is provided with an upwardly extending wall circumscribingly bounding a flow channel of generally rectangular shape. A liquid inlet port is disposed at a medial part of a first side of the flow channel, with the liquid outlet port at a medial part of a second side of the flow channel opposite the first side thereof. The liquid inlet port is joined in liquid flow communication with a liquid feed trough extending transversely across the first side of the flow channel, and the liquid outlet port is joined in liquid flow communication with a liquid collection trough extending transversely across the second side of the flow channel.

In this construction, a plurality of spaced-apart partitions extend upwardly from the floor of the flow channel between the liquid feed trough and the liquid collection trough. These partitions are of lesser height than the walls circumscribing the flow channel and are substantially parallel to one another, to define a series of sub-channels extending longitudinally between the liquid feed trough and the liquid collection trough. Both the liquid feed trough and the liquid collection trough are of progressively increasing depth from their respective medial portions to their marginal extremities.

Plates according to this prior patent may be utilized in stacked pairs to form enclosed flow channels within which filtration may take place in a highly efficient manner. Specifically, a first plate of the type broadly described above is paired with a structurally identical second plate positioned in inverted relationship to the first plate, such that the respective circumscribingly bounding walls of the first and second plates are in abutting sealing contact with one another. In this stacked arrangement, a filter element support of generally rectangular shape approximating the dimensions of the flow channel is interposed between the adjacent plates, with filter sheet elements between the support and each of the respective pair filter plates.

My prior U.S. Pat. No. 4,867,876 discloses a filter plate suitable for use with filter elements to form a stacked plate filter. In the stacked plate filter, pairs of such filter plates are mated with filter elements therebetween, to form flow channels wherein solids-containing liquid may be contacted with the filter sheet elements for filtration thereof to produce solids-reduced liquid, and permeate.

The filter plate of U.S. Pat. No. 4,867,876 has a generally planar shape with a substantially flat bottom surface. A top surface of the plate is provided with a first upwardly extending wall circumscribingly bounding a flow channel of generally rectangular shape. The flow channel in this prior design is circumscribingly bounded by a second upwardly extending wall interior to and of lesser height than the first circumscribingly bounding wall, the second wall being in spaced-relation to the outer wall along diagonally opposed L-shaped peripheral sections of the flow channel, each such L-shaped peripheral sections comprising a leg extending transversely across the flow channel for a major portion of the length thereof, and a leg dimension of the flow channel and communicating at its extremity with an opening extending through the plate, with the portions of the periphery of the flow channel not comprising such L-shaped sections comprising ridge elements extending between the first and second circumscribingly bounding walls.

A liquid inlet port is disposed at a first side of the flow channel in this prior design, with a liquid outlet port at a second side of the flow channel opposite the first side thereof.

The liquid inlet port in this prior filter plate is joined in liquid flow communication with a liquid feed trough interior to the second bounding wall and extending transversely across the first side of the flow channel. The liquid outlet port is joined in liquid flow communication with a liquid collection trough interior to the second bounding wall and extending transversely across the second side of the flow channel.

A plurality of spaced-apart partitions extend upwardly from the floor of the flow channel between the liquid feed trough and the liquid collection trough. Such partitions are substantially parallel to one another to define a series of subchannels extending longitudinally between the liquid feed trough and the liquid collection trough. These partitions preferably are of lesser height than the first (outer) wall circumscribing the flow channel and of substantially the same height as the second (inner) wall circumscribing the flow channel.

Plates of the foregoing type may be utilized in stacked pairs to form enclosed flow channels within which filtration may take place in a highly efficient manner. Specifically, a first plate of this type broadly described above may be paired with a plate of the type broadly described above may be paired with a corresponding second plate positioned in inverted relationship to the first plate, such that the respective first circumscribingly bounding walls of the first and second plates are abutting sealing contact with one another. In such stacked arrangement, a filter element of generally rectangular shape approximating the dimensions of the flow channel is interposed between the adjacent plates, suitably with its peripheral edges reposed on the second bounding wall. Such filter element is provided with an interior flow structure, whereby permeate entering the interior of the element is conveyed to the edge portions of the element for discharge into the aforementioned L-shaped peripheral sections of the flow channel between the respective first and second bounding walls. In an illustrative aspect, the filter element may comprise a foraminous support of generally rectangular shape approximating the dimensions of the flow channel, interposed between the adjacent plates, with filter sheet elements between the foraminous support and each of the respective filter plates.

In the operation of a stacked filter plate assembly of the type disclosed in prior U.S. Pat. No. 4,867,876, liquid introduced via the liquid inlet port enters the liquid feed trough and is laterally distributed from the associated portion of the feed trough to outer extremities thereof. The liquid flow is directed into the sub-channels to yield a longitudinal liquid cross-flow which is highly uniform over the full transverse extent of the flow channel, so that the full areal extent of the filter element is highly effectively utilized. As a result, the solids filtration capacity of the stacked plate assembly is substantially increased and the assembly is capable of significantly extended operation prior to regeneration of the filter, as compared to various prior art cross-flow plate and frame filters.

My prior U.S. Pat. No. 5,049,268 discloses a filter plate which may be used in invertedly facing pairs, with a sheetholder having filter sheets disposed on its respective faces, mounted between the facing filter plates. The filter plate is characterized by (a) a generally rectangular and generally planar shape with main top and bottom surfaces; (b) a first wall extending upwardly from said main top surface and circumscribingly bounding a flow channel area of generally rectangular shape thereon; (c) a second wall on said main top surface extending upwardly therefrom, said second wall being interior to and of lesser height than said first wall and in spaced relation to the first along diagonally opposed L-shaped peripheral sections of the flow channel area; (d) each L-shaped peripheral section comprising a leg extending transversely across the flow channel area for a major portion of the width thereof, and a leg extending longitudinally for a portion of the length of the flow channel area and communicating at its extremity with an opening extending through the plate, with peripheral portions of the flow channel area not comprising such L-shaped sections comprising ridges extending between the first and second walls; (e) an inlet port opening at a corner portion of the filter plate at a first end thereof, extending through the plate, interiorly positioned in a polygonal-shaped distribution basin on the main bottom surface of the plate, said distribution basin being bounded by generally linear side edges defining corners of the basin at respective intersections of the side edges; (f) an inlet trough opening extending through said plate and transversely across a major portion of the width of said flow channel area and along a first side edge of said distribution basin, such that said liquid inlet trough opening communicates said distribution basin on the main bottom surface of the plate with said flow channel area on the main top surface of the plate; (g) an outlet port opening at a corner portion of said plate diagonally opposite said inlet port opening, said outlet port opening extending through the plate, interiorly positioned in a polygonal-shaped collection basin on the main bottom surface of the plate, said collection basin being bounded by generally linear side edges defining corners of the collection basin at respective intersections of the side edges thereof; (h) an outlet trough opening extending through the plate and transversely across a major portion of the width of said flow channel area and long a first side edge of said collection basin, such that said outlet trough opening communicates said collection basin on the main bottom surface of the plate with said flow channel area on the main top surface of the plate; and (i) a plurality of transversely spaced-apart partitions extending upwardly from the floor of the flow channel area between the liquid feed trough and the liquid collection trough, said partitions being of substantially the same height as the second wall and substantially parallel to one another to define a series of channels between the partitions, extending longitudinally between the liquid feed trough and the liquid collection trough.

In one specific embodiment disclosed in prior U.S. Pat. No. 5,049,268, the liquid distribution basin and liquid collection basin each have quadrilateral shape, wherein each basin comprises: the port opening being disposed at a first said corner and the side edges intersecting at the first corner defining a first included angle w therebetween of from about 60° to about 110°; a second corner diagonally opposite the first corner, and the side edges intersecting at the second corner defining a second included angle x therebetween of from about 45° to about 90°; a third corner transversely adjacent the first corner and longitudinally adjacent the second corner, with the side edges intersecting at the third corner defining a third included angle y therebetween of from about 70° to about 135°; a fourth corner longitudinally adjacent the first corner and transversely adjacent the third corner, with the sides edges intersecting at the fourth corner defining a fourth angle z therebetween of from about 60° to about 90°; and the side edge extending transversely between the second and fourth corners also bounding the associated trough opening extending through the plate and communicating the basin with the flow channel area.

The filter plate disclosed in prior U.S. Pat. No. 5,049,268 is very highly efficient in effecting mass transfer operations, e.g., dewatering of aqueous biomass suspensions, desalting of proteins, and removal of secreted metabolites from cellular suspensions. Such filter plate may be readily formed as a unitary article by injection molding thereof from a variety of plastics materials, such as polypropylene, polysulfone, polyvinylchloride, etc., but due to the relatively complex geometric character of the filter plate, the injection molded plates are relatively expensive to produce.

Accordingly, it would be a significant advance in the art to provide a filtration article of a type which provides the superior mass transfer efficiency and utility of the filter plate disclosed in prior U.S. Pat. No. 5,049,268, but which is much more economical to produce than the filter plate and sheetholder of such prior U.S. Pat. No. 5,049,268.

It therefore is an object of the present invention to provide such an improved filtration article.

It is another object of the invention to provide a filter comprising a stack of improved filtration articles of such type.

It is another object of the invention to provide a method of making such improved filtration article, in a simple, efficient, and economical manner.

Other objects and advantages of the invention will be more fully apparent from the ensuing disclosure and appended claims.

SUMMARY OF THE INVENTION

The present invention relates generally to filtration cassettes, of a type comprising membrane filter sheets arranged in a multilaminate, peripherally bonded array, wherein the filter sheets alternate with foraminous (e.g., screen or mesh) permeate sheet elements, and ribbed retentate channel elements.

In another aspect, the present invention relates to cross-flow filters comprising a multiplicity of stacked filtration cassettes of the general type described in the preceding paragraph, as well as to a method of making such filtration cassettes.

In one particular aspect, the present invention relates to a filtration cassette comprising a multilaminate array of sheet members of generally rectangular and generally planar shape with main top and bottom surfaces, wherein the sheet members include in sequence in said array a first retentate sheet, a first filter sheet, a permeate sheet, a second filter sheet, and a second retentate sheet, wherein each of the sheet members in said array has at least one inlet basin opening at one end thereof, and at least one outlet basin opening at an opposite end thereof, with permeate passage openings at longitudinal side margin portions of the sheet members;

each of the first and second retentate sheets having at least one channel opening therein, extending longitudinally between the inlet and outlet basin openings of the sheets in the array, and being compression bonded to an adjacent filter sheet about peripheral end and side portions thereof, with their basin openings and permeate passage openings in register with one another and the filtrate passage openings of each of the retentate sheets being circumscribingly compression bonded to the adjacent filter sheet, and with a central portion of each of the retentate sheets and adjacent filter sheets being unbonded to permit permeate contacting the retentate sheet to flow through the filter sheet to the permeate sheet; and each of the filter sheets being secured at its peripheral portions on a face thereof opposite the retentate sheet, to the permeate sheet.

In another particular aspect, the present invention relates to a filtration cassette comprising a multilaminate array of sheet members of generally rectangular and generally planar shape with main top and bottom surfaces, wherein the sheet members include:

a first compressible retentate sheet of suitable material, e.g. polysulfone, polyethersulfone, polycarbonate, urethane, silicone, or other compressible material of construction, having (i) at least one longitudinally extending rib or partition element, such partition element(s) when provided in multiple configuration being transversely spaced apart from one another and being of substantially the same height and substantially parallel to one another to define a single or a series of channels between the partitions, extending longitudinally between the respective inlet and outlet basin openings of associated filter elements and permeate sheet members, on both faces thereof, (ii) filtrate passage openings at side portions of the sheets, and (iii) the retentate sheet aligned to the first sheet of filter material at respective end and side portions thereof, with the basin openings and filtrate passage openings of the associated sheet members in register with one another and the filtrate passage opening of the retentate sheet member being circumscribingly compressed to the first sheet of filter material, and with a central portion of the first sheet of filter material and the retentate sheet member being unbonded to permit permeate contacting the retentate sheet member to flow through the first sheet member of filter material to the foraminous permeate sheet member;

a first sheet member of filter material having (i) multiple basin openings, of a suitable shape, e.g., polygonal, semicircular, or sector shape, at each of opposite end portions of the sheet member defining respective inlet and outlet passages, each basin being bounded by generally linear side edges defining corners of the basin at respective intersections of the side edges, and (ii) filtrate passage openings at the side portions of the sheet member, wherein the first sheet member of filter material is bonded to the foraminous permeate sheet member at their respective end and side portions, with their basin openings and filtrate passage openings in register with one another and the basin openings being circumscribingly bonded at respective end portions of the first sheet member of filter material and the formaminous permeate sheet member, and with a central portion of the first sheet member of filter material and the formaminous permeate sheet member being unbonded so as to define a central portion permeate channel of the formaminous permeate sheet communicating with the filtrate passages in the first sheet member of filter material and in the formaminous permeate sheet member;

a formaminous permeate sheet member of screen or mesh material, having (i) multiple basin openings of suitable shape at each of opposite end portions of the sheet member defining respective inlet and outlet passages, each basin being bounded by generally linear side edges defining corners of the basin at respective intersections of the side edges, and (ii) filtrate passage openings at the side portions of the sheet member;

a second sheet member of filter material having (I) multiple basin openings at each of opposite end portions of the sheet member defining respective inlet and outlet passages, each basin being bounded by generally linear side edges defining corners of the basin at respective intersections of the side edges, and (ii) filtrate passage openings at the side portions of the sheet member, wherein the second sheet member of filter material is compression sealed to the retentate sheet member at their respective end and side portions, with their basin openings and filtrate passage openings in register with one another and the filtrate passage opening of the retentate sheet member being compression sealed to the second sheet member of filter material, and with a central portion of the second sheet member of filter material and the retentate sheet member being unbonded to permit permeate contacting the retentate sheet member to flow through the second sheet member of filter material; and a second compressible retentate sheet member of suitable material, e.g. polysulfone, polyethersulfone, polycarbonate, urethane, silicone, having (i) at least one longitudinally extending rib or partition element, provided that when mulitple partition elements are employed, the partition elements are transversely spaced-apart from one another, such partition elements being of substantially the same height and substantially parallel to one another, to define a single channel or a series of channels between the partitions, extending longitudinally between the respective inlet and outlet basin openings of the filter elements and permeate sheet members, on both faces thereof, (ii) filtrate passage openings at the side portions of the sheet member, and (iii) the retentate sheet compression sealed to the second sheet of filter material at respective end and side portions thereof, with their basin openings and filtrate passage openings in register with one another and the filtrate passage opening of the retentate sheet member being compression sealed to the second sheet member of filter material, and with a central portion of the first sheet member of filter material and the retentate sheet member being unbonded to permit permeate contacting the retentate sheet member to flow through the second sheet member of filter material to the foraminous permeate sheet member.

As used hereinafter, the term "sheet member" employed in reference to the various laminae of the cassette—the cassette being the stack of generally planar sheet members forming an operative mass transfer unit when coupled to fluid supply, retentate and filtrate flow means—will be variously referred to as simply "sheet." It will therefore be noted that the term "sheet" will denote the generally planar members of the cassette, the cassette thus comprising an assembly of permeate sheets, filter sheets, and retentate sheets, coupled to one another in such manner as to permit flow of the fluid to be separated through the flow channel(s) of the device, for mass transfer involving passage of the filtrate through the filter sheets, and retention of the retentate on the side of the filter sheet opposite the side from which the filtrate emerges. The term "compressible" in reference to the retentate sheet or other structural feature or sheet member of the present invention means that such component or member is compressively deformable by application of load or pressure thereon.

The above-described filtration cassette of the invention comprises a "base sequence" of elements, defined as a sequence of sheet elements constituting a compressible retentate sheet (hereafter designated by the symbol "CR"), a filter sheet (hereafter designated by the symbol "F"), a foraminous permeate sheet (hereafter designated by the symbol "P"), a second filter sheet ("F"), and a second compressible retentate sheet ("CR"), thereby providing a sequence of sheet elements, CR/F/P/F/CR.

The base sequence of sheet elements may be utilized in construction of filters comprising a plurality of filtration cassettes, wherein the compressible retentate sheet is utilized to seal the top and bottom elements of a plurality of filtration cassettes of a sequence, comprising compressible retentate sheet "CR", filter sheet "F", foraminous permeate sheet P, filter sheet "F", non-compressible retentate sheet "R", filter sheet "F", foraminous permeate sheet P, filter sheet "F", and compressible retentate sheet "CR". An illustrative stacked cassette filter according to the invention may for example feature the sheet sequence CR/F/P/F/R/F/P/F/R/F/P/F/CR, comprising a first compressible retentate sheet, two base sequences of sheets FPFR in a repetitive sequence, and a second compressible retentate sheet. In all repetitive sequences, other than a single cassette base sequence, the following relationship is observed: where X is the number of filter sheets F, the quantity 0.5X−1 is the number of non-compressible retentate sheets R, and the quantity 0.5X is the number of foraminous permeate sheets P, with two compressible retentate sheets being utilized to seal the top and bottom extremeties of the intervening sequence.

Thus, it is possible to utilize a large number of base sequence cassettes in a repetitive sequence, to provide a stacked cassette filter of the desired mass transfer area. Many configurations are possible. It is feasible in some instances, e.g., for mass transfer studies and system quantitation, to utilize a single cassette comprising the base sequence CR/F/P/F/CR wherein the outermost retentate sheets in the sequence are compression-sealed at their outer faces to an end plate accommodating removal of permeate from the filtrate passage openings of the constituent sheet members in the cassette.

The sheets of filter material used in the cassette article of the present invention may be of any suitable porosity rating. As used herein, the porosity rating of a sheet of filter material is the smallest particle size which cannot pass through the pores of the filter material. Typical porosity ratings are expressed in molecular weight (MW) and micrometer units, e.g., a 2 micron filter media sheet being a material which will pass particles smaller than 2 microns in diameter through the pores of the material, while particles larger than 2 microns will not be passed through the filter material, and as a further example, a 10,000 MW filter media sheet being a material which will pass particles smaller than 10,000 MW in diameter through the pores of the material, while particles larger than 10,000 MW will not be passed through the filter material.

In one preferred embodiment of the cassette article of the invention, a foraminous retentate sheet is provided with a plurality of transversely spaced-apart, longitudinally extending ribs or partitions, extending upwardly from (the central portion of) each of the main top and bottom faces of the formaminous retentate sheet, such ribs or partitions being of substantially the same height and substantially parallel to one another to define a series of channels between the partitions, extending longitudinally between the respective basin openings of the retentate sheet, on both faces thereof. The adjacent filter sheets may be further bonded to the outer extremities of the ribs or partitions, and the ribs or partitions may be formed of any suitable material, e.g., a flexible resilient adhesive bonding medium, such as a urethanes, epoxy or silicone adhesive sealant medium, e.g., applied in a "bead" in the longitudinal direction of the retentate sheet on both main top and bottom faces thereof.

As used herein, the term "bonded" in reference to adjacent sheets in the multilaminate cassette means that the adjacent sheets are secured to one another in such manner as to prevent flow of the material being, processed, e.g., the feed material to be separated, as well as component materials therefrom (filtrate or permeate, as well as retentate), from flowing through such secured areas or between the adjacent sheets at such secured areas. Preferably, the bonding is carried out with a suitable adhesive or sealant medium, e.g., a urethane, epoxy, cyanoacrylate, or silicone adhesive material, which fills the interstices of the formaminous sheet in the bonded pair of sheets, and adhesively joins one of the adjacent sheets to the other in the bonded areas.

As used herein, the term "compressive bonding" and "compressively bonded" refer to bonding and bonding operations in which the structure being bonded is subjected to a compressive load or force, for sufficient time and under sufficient period to effect the bonding securement of the structure. The invention may for example be carried out with bonding of sheets in the multilaminate array to one another with cyanoacrylate or other "fast" adhesives, or alternatively the adhesive or sealant medium may require extended cure at ambient temperature or other appropriate cure conditions, and it may be advantageous to conduct such cure with the laminate structure in a fixture or other assembly in which the compressive bonding is effectively completed. Compressive bonding of laminae in the practice of the invention is highly desirable, in order to assure the leak-tightness and structural integrity of the resulting multilaminate assembly of the cassette.

In one specific embodiment of the cassette article of the invention, the inlet and outlet basins each comprise two quadrilateral openings, wherein each basin opening comprises:

side edges intersecting at a first corner of the basin opening defining a first included angle w therebetween of 90°;

a second corner diagonally opposite said first corner, and the side edges intersecting at such second corner defining a second included angle x therebetween of 90°;

a third corner transversely adjacent the first corner and longitudinally adjacent the second corner, with the side edges intersecting at the third corner defining a third included angle y therebetween of 90°;

a fourth corner longitudinally adjacent the first corner and transversely adjacent the third corner, with the sides edges intersecting at the fourth corner defining a fourth angle z therebetween of 90°.

In another embodiment of the cassette article of the invention, the inlet and outlet basins each comprise four quadrilateral openings, wherein each basin opening comprises:

side edges intersecting at a first corner of the basin opening defining a first included angle w therebetween of 90°;

a second corner diagonally opposite said first corner, and the side edges intersecting at such second corner defining a second included angle x therebetween of 90°;

a third corner transversely adjacent the first corner and longitudinally adjacent the second corner, with the side edges intersecting at the third corner defining a third included angle y therebetween of 90°;

a fourth corner longitudinally adjacent the first corner and transversely adjacent the third corner, with the sides edges intersecting at the fourth corner defining a fourth angle z therebetween of 90°.

Each sheet member in the cassette broadly described hereinabove may suitably comprise filtrate passage openings at the side portions (margins) of the sheet member.

In a specific aspect of the invention, each of the foraminous permeate and foraminous retentate sheets may constitute a foraminous material of from about 80 to about 300 mesh size. Each of the foraminous permeate and retentate sheets may for example comprise a woven polymeric mesh, e.g., of a material selected from the group consisting of polyester, polypropylene, nylon, fluorocarbon polymers such as polytetrafluoroethylene, polyethylene, and polysulfone, and composites comprising one or more of such materials.

The permeate and retentate sheets alternatively may comprise a nonwoven material, if of suitable foraminous character, or alternatively may comprise a sintered metal matrix, or other structural element of the desired porosity and permeability characteristics.

The filter sheets used in the filtration cassette of the present invention may be of any suitable materials, such as a material selected from the group consisting of cellulose, polyphenylene oxide, polysulfone, cellulose nitrate, cellulose acetate, regenerated cellulose, polyether amide, polyphenylene oxide/polysulfone blends, mixed esters of cellulose, and polyether sulfone.

In one specific embodiment of the cassette article of the invention, the inlet and outlet basins of the sheet members are structurally reinforced by radio frequency (RF) welding of urethane or other suitable material such as ethylvinylacetate, silicone, and EPDM. In a particularly preferred specific embodiment of the invention, a first assembly consisting of a first filter sheet, foraminous permeate sheet, and second filter sheet are urethane bonded and then die cut to form a first cutout of inlet and outlet basins. The longitudinal ends of the first assembly then are covered on both sides (main faces) thereof with a thin sheet of urethane which completely overlays the inlet and outlet basins. The first assembly with the respective laminae, in the sequence of: urethane sheet, filter sheet, foraminous permeate sheet, filter sheet, and urethane sheet, then is RF welded to form a second assembly. The RF welding fuses the two sheets of urethane inside the inlet and outlet basins resulting in an encapsulation of the inlet and outlet basins. The second assembly then is die cut a second time, to create an opening at the inlet and outlet basins which is dimensionally smaller then the first cut.

The resulting newly formed inlet and outlet basins are now entirely encapsulated and reinforced by the fused urethane sheets. This specific technique is a substantial improvement to existing stacked cassette elements because it prevents the delamination of ultrafiltration membranes. Numerous membrane types, especially ultrafiltration membranes and reverse osmosis membranes, are cast (manufactured) as a skin layered on a support structure. In use, the turbulence associated with the fluid in the inlet and outlet basins results in delamination and membrane cassette failure. The aforementioned encapsulation procedure reinforces and seals the exposed skin of two part membrane structures wherein the membrane and cassette life is greatly extended. Additionally, the reinforced inlet and outlet basins can be operated at higher velocities for improved operation and cleaning without the occurrence of membrane delamination.

Another aspect of the present invention relates to a stacked cassette cross-flow filter comprising cassette articles of the type described above.

Still another aspect of the present invention relates to a pair of end plates or manifold assembly in which the cassettes are secured for operation.

Other aspects and features of the present invention will be more fully apparent from the ensuing disclosure and appended claims.

DETAILED DESCRIPTION OF THE INVENTION, AND PREFERRED EMBODIMENTS THEREOF

Figure 1:
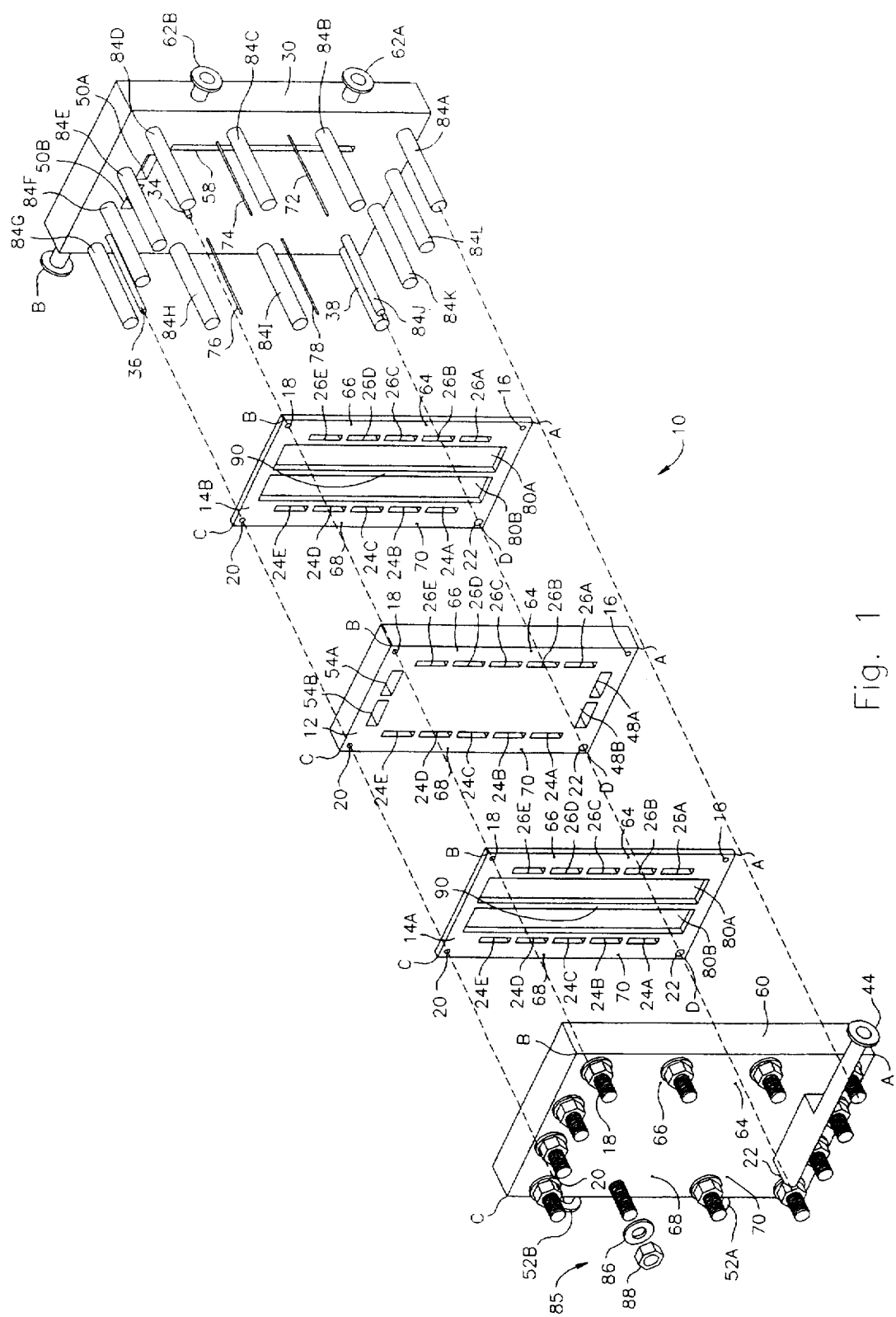
FIG. 1 is a perspective view of a filter assembly comprising a filtration cassette according to one embodiment of the present invention with compressible end gaskets and end plates.

The disclosure of prior copending U.S. patent application Ser. No. 29/019,362 filed Mar. 1, 1994 hereby is incorporated herein by reference, in its entirety.

The filter cassette article of the present invention is adapted to be employed in stacked arrays to form a stacked cassette filter assembly in which the base sequence of compressible retentate sheet (CR), filter sheet (F), formaminous permeate sheet (P), filter sheet (F), and compressible retentate sheet (CR) may be repeated in the sequence of sheets in the filter assembly as desired, e.g., in a repetitive sequence of compressible retentate sheet (CR), filter sheet (F), retentate sheet (R), filter sheet (F), formaminous permeate sheet (P), filter sheet (F), retentate sheet (R), filter sheet (F), formaminous permeate sheet (P), filter sheet (F), retentate sheet (R), filter sheet (F), compressible retentate sheet (R). Thus, the filter cassette of a desired total mass transfer area is readily formed from a stack of the repetitive sequences. In all repetitive sequences, except for a single unit sequence, the following relationship is observed: where X is the number of filter sheets, 0.5X−1 is the number of retentate sheets, and 0.5X is the number of permeate sheets, with two compressible retentate sheets being provided at the outer extremeties of the stacked sheet array.

The filter sheets, and the retentate and permeate sheets employed therewith, may be formed of any suitable materials of construction, including, for example, polymers, such as polypropylene, polyethylene, polysulfone, polyethersulfone, polyetherimide, polyimide, polyvinylchloride, polyester, etc.; nylon, silicone, urethane, regenerated cellulose, polycarbonate, cellulose acetate, cellulose triacetate, cellulose nitrate, mixed esters of cellulose, etc.; ceramics, e.g., oxides of silicon, zirconium, and/or aluminum; metals such as stainless steel; polymeric fluorocarbons such as polytetrafluoroethylene; and compatible alloys, mixtures and composites of such materials.

Preferably, the filter sheets and the retentate and permeate sheets are made of materials which are adapted to accommodate high temperatures and chemical sterilants, so that the interior surfaces of the filter may be steam sterilized and/or chemically sanitized for regeneration and reuse, as "steam-in-place" and/or "sterilizable in situ" structures, respectively. Steam sterilization typically may be carried out at temperatures on the order of from about 121° C. to about 130° C., at steam pressures of 15–30 psi, and at a sterilization exposure time typically on the order of from about 15 minutes to about 2 hours, or even longer. Alternatively, the entire cassette structure may be formed of materials which render the cassette article disposable in character.

The end plates used with the cassette articles of the invention to form a unitary filter assembly may be formed of any suitable materials of construction, including, for example, stainless steel or other suitable metal, or polymers such as polypropylene, polysulfone, and polyetherimide.

FIG. 1 is a perspective view of a cross-flow filter 10 comprising a cassette article 12 according to one embodiment of the present invention. The cassette is of a multilaminate construction, comprising a plurality of sheets as described hereinafter in greater detail, peripherally bonded to one another at their end and side margins.

For ease of description in the ensuing discussion, the respective corners of the cassette as shown in FIG. 1 are lettered consecutively, beginning at the lower right-hand corner A as shown and, proceeding counterclock-wise, including upper right-hand corner B, upper left-hand corner C, and lower left-hand corner D.

In the vicinity of these consecutive corners A, B, C, and D of the cassette are provided openings 16, 18, 20, and 22, respectively, which extend through the cassette and are employed for mounting of the cassette on rods of diameter closely approximate but slightly smaller than the respective openings. In this respect, it is to be noted that opening 22 is of larger size (diameter) than the remaining openings 16, 18, and 20. The purpose of such disparity in opening size is to provide a "keying" feature whereby the proper alignment of the plate is secured, since only opening 22 will fit over a large-sized rod of corresponding diameter, whereas openings 16, 18, and 20 will not accommodate passage over such a large-sized rod.

Other features or structures may be employed for the same purpose, viz., of keying the cassette to a predetermined proper orientation, in place of the different sized opening 22 relative to the remaining same-sized corner openings 16, 18, and 20. For example, one of the respective corner openings may be of a different shape than the others, e.g., square or triangular in cross-section, rather than circular. Alternatively, the corner profile of one corner of the cassette may be notched or differently shaped in relation to the other corners, to provide a readily visibly discernible keying or orientational structure of the cassette article.

The filtration cassette 12 is provided at its respective side margins with openings 64, 66, 68, and 70 which are smaller than openings 16, 18, and 20 and which are employed for keeping the compressible retentate sheet in place.

The filtration cassette 12 also is provided at its respective side margins, at the mid-section of the longitudinally extending cassette, with openings 24 A, B, C, D, E and 26 A, B, C, D, E extending through the cassette. These openings may be employed for egress of permeate produced in the filtration operation when the cassette is deployed in the stacked cassette filter assembly illustrated, and/or otherwise for accommodating ingress/egress of a selected fluid, such as steam or other sterilant fluid for effecting cleaning and regeneration of the filter, or a secondary fluid for mass transfer contacting with a primary fluid passage through the filter.

This filter 10 comprises a base including a mounting plate 30 having vertically upwardly extending rods 34, 36, and 38 at its respective corner portions as shown. Each of the rods 34, and 36 are of the same diameter, while the fourth rod 38 is of larger diameter, to provide the plate orientation keying structure, which will ensure that the constituent plates of the filter assembly are assembled in the proper orientation, since the corresponding rod mounting openings 18 and 20 in the cassettes, e.g., cassette 12, are of the same diameter, accommodating the smaller diameter rods, while the third rod mounting opening 22 is of larger diameter, to accommodate rod 38. Thus, by providing a rod of larger diameter, and forming the cassettes 12 with correspondingly shaped openings, the proper registration of the cassette openings with the proper rods is assured, resulting in correct orientation of the respective stacked filtration cassettes in the array.

This filter 10 comprises a base including a mounting plate 30 having upwardly extending rods 72, 74, 76, and 78 correspond to openings 64, 66, 68, and 70 for mounting and allignment of the compressible retentate sheets 14A and 14B.

It will be appreciated from the foregoing that any other cassette orientation registration device may be employed to ensure to correct positioning of the successive stacked filtration cassettes on the mounting plate 30. For example, the cassettes are oriented with their successive notches superposed with respect to one another. Alternatively, the cassette itself may be embossed, etched, or otherwise manufactured with an orientational device, e.g., a raised protrusion in the shape of an arrow, to indicate the correct orientation of the filtration cassettes when stacked on the mounting plate 30. Although only one filtration cassette is illustratively shown in the FIG. 1 embodiment, it will be recognized that one or a plurality of cassettes may be employed to form a filter in accordance with the present invention.

Between the cassette 12 and mounting plate 30, there is provided a compressible retentate sheet 14B which is equipped with openings to accommdate its positioning over the respective rods 34, 36, 38, 72, 74, 76, and 78 so that the compressible retentate sheet seals the bottom surface of the cassette 12. The retentate sheets in the multilaminate array may for example have a thickness between 0.125 mm and 6.0 mm, and the other sheets in the array may have correspondingly dimensioned thicknesses appropriate to the mass transfer operation being conducted with the cassette.

Overlying the cassette 12 in the exploded array of FIG. 1 there is provided a compressible retentate sheet 14A which is equipped with openings to accommdate its positioning over the respective rods 34, 36, 38, 72, 74, 76, and 78 so that the compressible retentate sheet seals the top surface of the cassette 12.

Overlying the cassette 12 in the exploded array of FIG. 1 is an upper end plate 60, which is provided with suitable openings 18, 20, 22, 64, 66, 68, and 70 accommodating the insertion therethrough of the rods 34, 36, 38, 72, 74, 76, and 78.

Overlying the cassette 12 in the exploded array of FIG. 1 is an upper end plate 60, which as shown is suitably engaged by mechanical fastener assemblies 85, comprising washer 86 and lock-nut 88, which threadably engages the complementarily threaded upper ends of the respective rods 84A . . . 84K, and 84L.

At the upper left-hand corner portion C of the mounting plate 30 shown in FIG. 1, adjacent to rod 36, there is provided a liquid outlet conduit 8 in flow communication with openings 50A and 50B extending through the end plate 30 and communicating with the quadrilateral-shaped collection basins 54A and 54B of the cassette.

The mounting plate 30 also is provided at its right-hand side margins, at the distal section of the longitudinally extending plate, with permeate collection trough 58 which is in flow communication with permeate outlet conduits 62A and 62B. This is employed for egress of permeate produced in the filtration operation (and issuing from filtrate or permeate opening 26 A, B, C, D, E in cassette 12) and/or otherwise for accommodating ingress/egress of a selected fluid, such as steam or other sterilant fluid for effecting cleaning and regeneration of the filter.

At the lower right-hand corner portion A of the end plate 60 shown in FIG. 1 there is provided a liquid inlet conduit 44 in flow communication with openings 46A and 46B (not shown) extending through the end plate 60 and communicating with the quadrilateral-shaped collection basins 48A and 48B of the cassette.

The end plate 60 also is provided at its left-hand side margin, at the near-section of the longitudinally extending plate, with permeate collection trough 56 (not shown) in flow communication with permeate outlet conduits 52A and 52B. This conduit is employed for egress of permeate produced in the filtration operation (and issuing from filtrate or permeate opening 24 A, B, C, D, E in cassette 12), and/or otherwise for accommodating ingress/egress of a selected fluid, such as steam or other sterilant fluid for effecting cleaning and regeneration of the filter.

The cassette 12 shown in FIG. 1 has a quadrilateral-shaped feed distribution trough, in which liquid entering in feed liquid conduit 44 issues from feed liquid openings 46A and 46B (not shown) therein and is distributed in the feed distribution basin 48A and 48B, from which it passes longitudinally through the cassette 12, in a flow channel provided between the retentate sheet and adjacent filter sheets, as hereinafter more fully described. In the flow channel, the permeate components of the feed material passes through the filter sheets adjacent to the retentate sheet, and flows into next-adjacent permeate channels, from which the permeate flows to openings 24 A, B, C, D, E and 26 A, B, C, D, E. The retentate then issues from an opposite end portion of the central flow channel of the cassette into the collection basins 54A and 54B, from which the retentate is discharged from the filter through openings 50A and 50B into liquid conduit 8.

It will be appreciated that the permeate openings 24 A, B, C, D, E and 26 A, B, C, D, E may, as previously described, be coupled to a flow circuit including a second mass transfer medium which is to be passed in mass transfer relationship to the primary feed material stream entering the filter in conduit 44. By such arrangement, mass transfer is able to be carried out in both directions across the filter sheets in the cassette. Alternatively, the filter may be used as shown, with the openings 24 A, B, C, D, E and 26 A, B, C, D, E being used for discharge of permeate. It will be recognized that instead of two permeate conduits 62A and 62B on the mounting plate 30, and two permeate conduits 52A and 52B on the end plate 60, both permeate outlet conduits may be provided on mounting plate 30, or on end plate 60, or alternatively, both plates may feature any number of permeate discharge conduits secured thereto and in communication with the permeate openings of the cassette(s).

Figure 2:
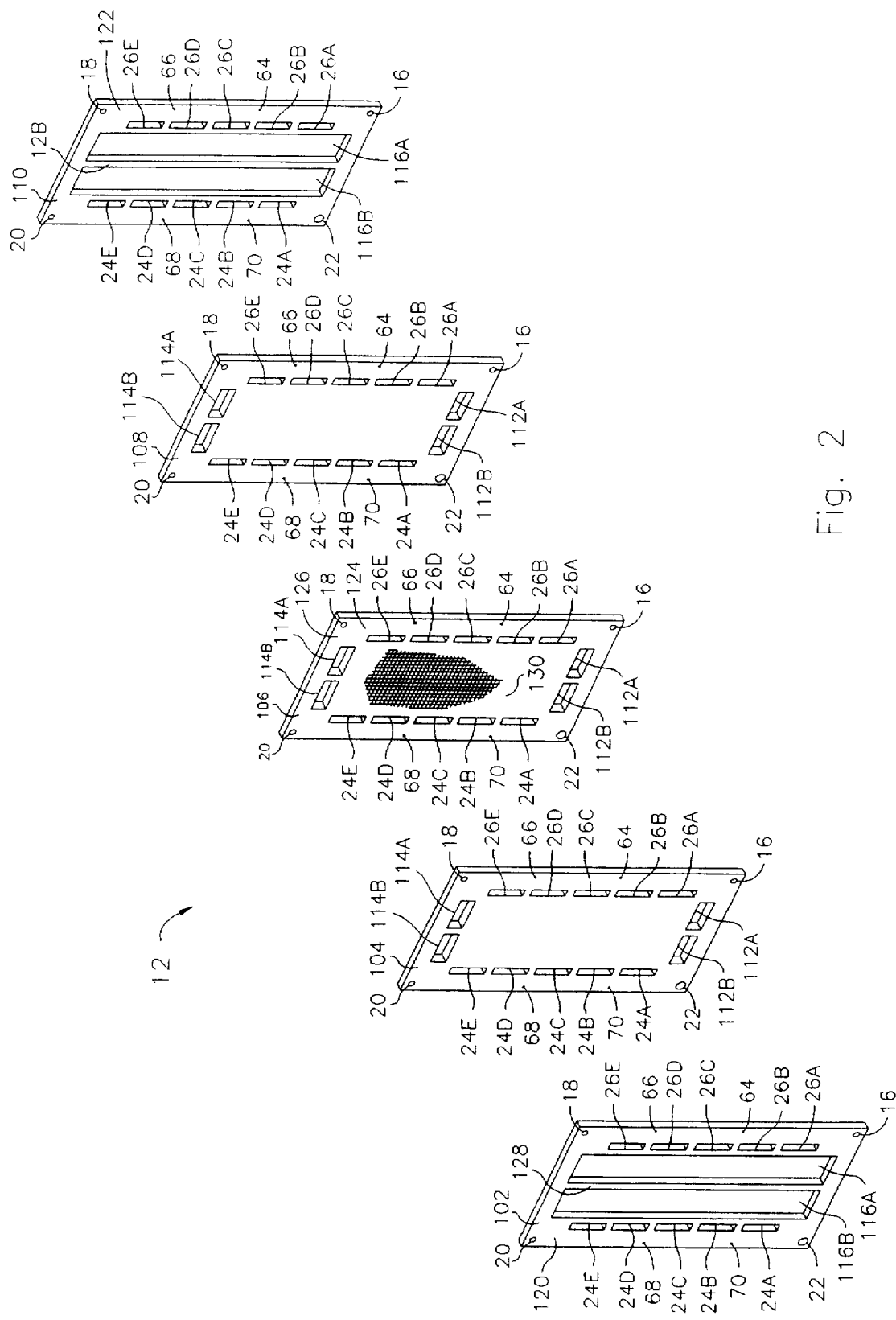
FIG. 2 is an exploded perspective view of a filtration cassette according to one embodiment of the present invention.

FIG. 2 is an exploded perspective view of a cassette 12 employed in the FIG. 1 filter, and comprising, a compressible retentate sheet 102, a filter sheet 104, a foraminous permeate sheet 106, a filter sheet 108, and a compressible retentate sheet 110, as constituent sheets in the multilayer array.

As shown, each of the constituent filter sheets 104, 106, and 108 has a generally quadrilateral-shaped cut-out opening 114A and 114B at one end thereof, and a similar cut out opening 112A and 112B at the opposite end thereof, and each of the sheets is provided with corner openings 16, 18, 20, 22, 64, 66, 68, and 70.

As shown, each of the compressible retentate sheets 102 and 110 have quadrilateral retentate channels 116A and 116B.

Each of sheets is generally co-extensive in areal extent with the others, and when consolidated into a unitary cassette article, the cutout openings 112A and 112B and 114A and 114B and retentate channels 116A and 116B in each of the respective sheet elements are in registration, as are the rod openings 16, 18, 20, 22, 64, 66, 68, and 70. The sheets are each bonded at their side and end extremities to the next adjacent sheet in the cassette, and the retentate sheet 102 is bonded at its peripheral region 120 to the corresponding peripheral region of filter sheet 104, and in like manner the retentae sheet 110 is bonded at its peripheral portion 122 to filter sheet 108. Permeate sheet 106 is bonded at its outer periphery 124 on its top face to filter sheet 104, and the permeate sheet at its bottom face is bonded along its peripheral region 126 to filter sheet 108.

On the retentate sheets, a longitudinally extending, transversely spaced-apart rib 128 is provided, extending from the inlet basin opening 112 and 112B to the collection basin opening 114A and 114B.

The permeate sheet 106 is suitably bonded to the adjacent filter sheets (108 and 104, respectively) in such manner as to leave an unbonded central area 130 on permeate sheet 106 which communicates with the filtrate or permeate openings 24 A, B, C, D, E and 26 A, B, C, D, E whereby filtrate is readily removed from the cassette in use.

Figure 3:
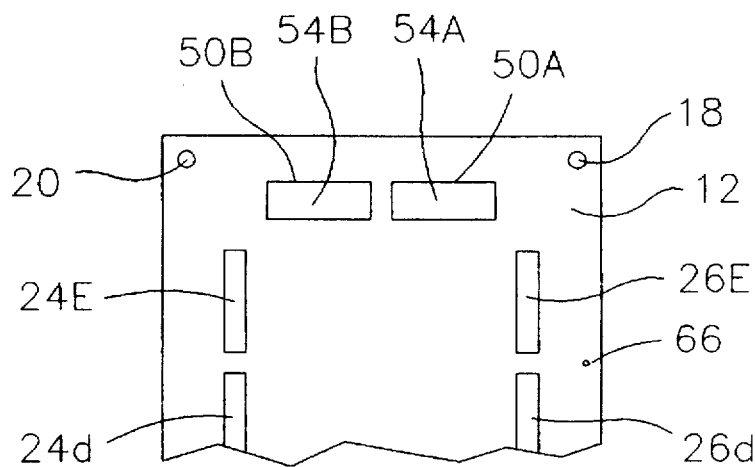
FIG. 3 is a top plan view of a portion of a filtration cassette, featuring two quadrilateral-shaped basins.

FIG. 3 is a top plan view of a portion of a cassette article 12, wherein the collection basin is composed of two quadrilateral shaped basins 54A and 54B.

Figure 4:
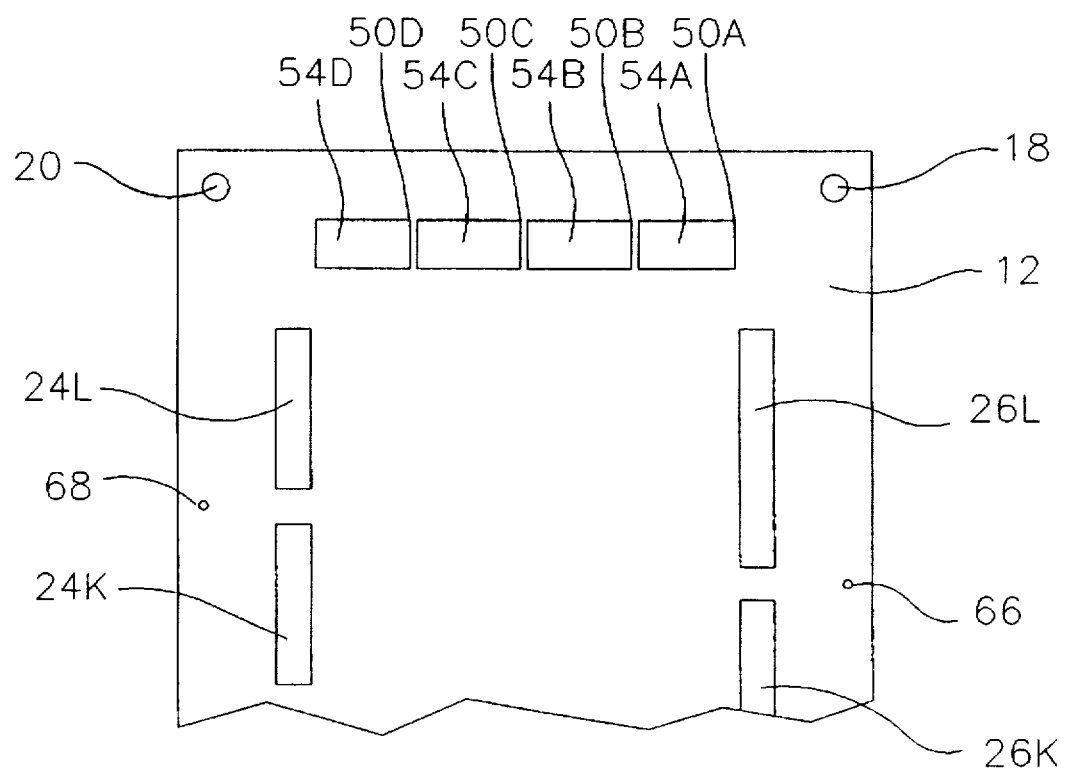
FIG. 4 is a top plan view of a portion of a filtration cassette according to another embodiment of the invention, featuring four quadrilateral-shaped basins.

FIG. 4 is a top plan view of a cassette 12 according to another embodiment of the invention featuring four quadrilateral shaped basins 54A, 54B, 54C, and 54D. Shown in dashed line representation in the basin is the liquid collection conduit 50A, 50B, 50C, and 50D, denoting the position of the liquid withdrawal conduit relative to the basin structure. It wil be recognized that the inlet distribution basins corresponding to the outlet collection basin shown in FIGS. 3 and 4, respectively, are similarly configured, with respect to their shape and component angles, relative to the same cassette article, although the distribution and collection basins could in some applications advantageously be hemispherical or of different shape and size characteristics.

Although the quadrilateral shape of the respective liquid distribution basins 48A and 48B and collection basins 54A and 54B may be widely varied in the broad practice of the present invention, as regards the specific values of the corner angles of such basins, the specific shape and angles shown in FIGS. 3 and 4 are most preferred to facilitate uniformity of flow path length for liquid across the entire areal extent of the respective basins and flow channel area, i.e., a generally uniform velocity profile of the fluid flowing longitudinally across the flow channel area of the cassette.

In the filtration casette shown in FIG. 4, wherein the distribution basins each comprise four quadrilateral sub-basins 54A, 54B, 54C, and 54D, each sub-basin suitably comprises: side edges intersecting at a first corner defining a first included angle a therebetween of 90°; side edges intersecting at a second corner defining an included angle b therebetween of from about 90°; a third corner transversely opposite the first corner, with the side edges intersecting at the third corner defining an included angle c therebetween of 90°; and a fourth corner transversely opposite the third corner, with the side edges intersecting at the fourth corner defining an included angle d therebetween of 90°.

In like manner the distribution and collection basins could in some applications advantageously be hemispherical or of different shape and size characteristics.

The filter cassette of the present invention may be fabricated in any suitable manner, including casting, injection molding, dielectric bonding, solvent bonding, adhesive bonding, etc., the specific method of fabrication depending on the material of construction and the desired end use. For example, polysulfone is a preferred material of construction for the filter sheets, alternating with polysulfone retentate sheets, and foraminous polypropylene permeate sheets, and bonded by urethane or cyanoacrylate adhesive.

In one particularly preferred embodiment of the invention, the cyanoacrylate adhesive Super Bonder #4981 from Loctite Corporation, Newington, Conn. is utilizedas the adhesive bonding medium for construction of the cassette.

In another particularly preferred embodiment of the invention, a two part urethane CONATHAMES #DPST-20256(part A and part B) Conap, Inc., Olean, N.Y. is employed as the cassette bonding material.

When polysulfone, polypropylene, and urethane are utilized as materials of construction, dielectric bonding may suitably be employed as the method of fabrication.

Alternatively, when polypropylene, polypropylene, and cyanoacrylates are utilized as the materials of construction, wet bonding may suitably be employed as the method of fabrication.

Figure 5:
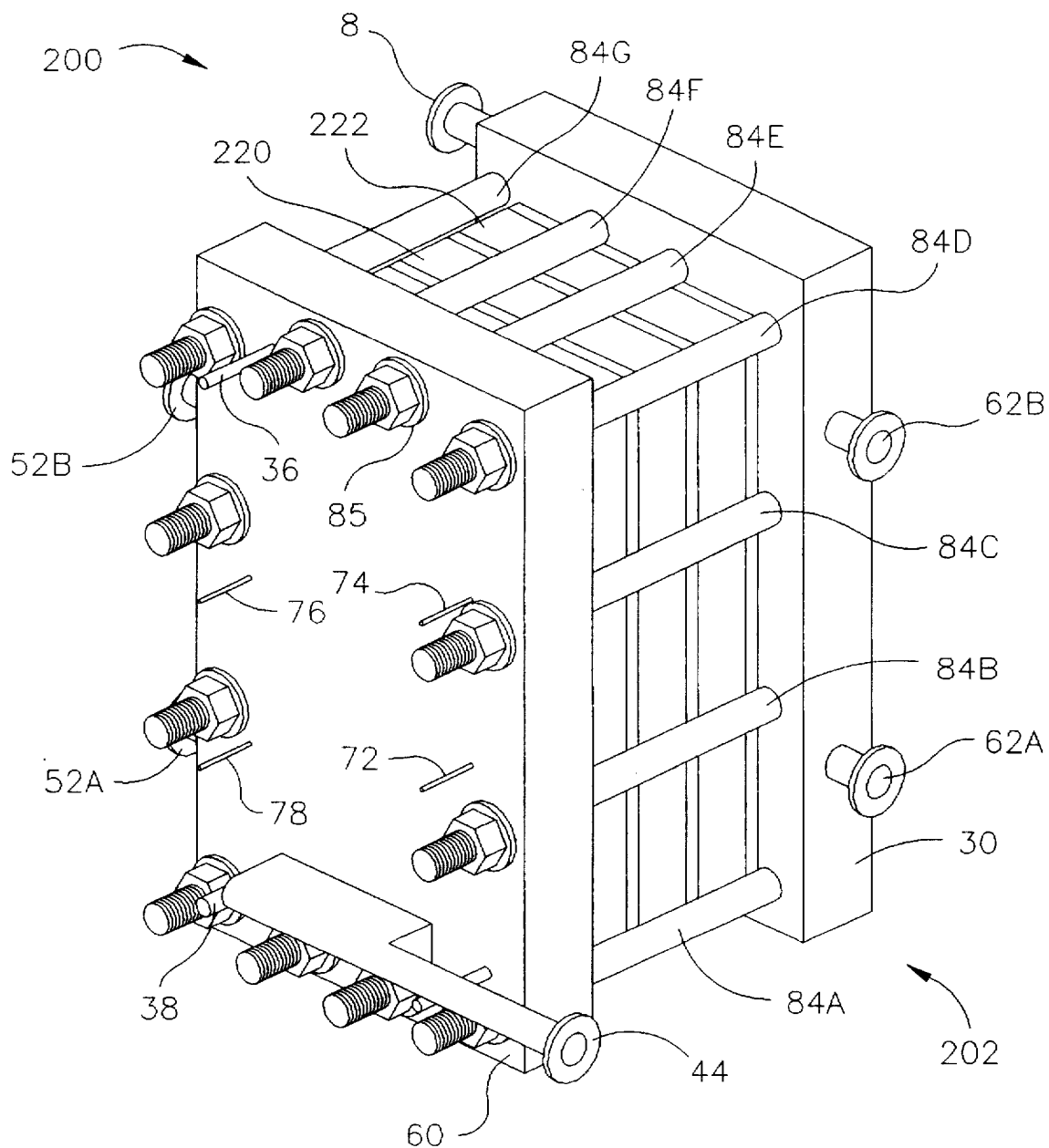
FIG. 5 is a perspective elevation view of a filter comprising a multiplicity of cassette articles according to the present invention.

FIG. 5 shows a perspective elevation view of a filter according to one embodiment of the invention, utilizing a plurality of cassettes according to the invention, to form a stacked cassette array.

This stacked cassette filter 200 comprises a base 202 including a mounting plate 30 having vertically upwardly extending rods 34, 36, 38, 72, 74, 76, and 78 at the respective corner and side portions as shown. Each of the rods 34 and 36 is of the same diameter, while the third rod 38 is of larger diameter, to provide a cassette orientation keying structure, which will ensure that the constituent cassettes and compressible retentate sheets of the filter assembly are assembled in the proper orientation, with the corresponding rod mounting openings in the cassette being appropriately sized for such rods. Rods 72, 74, 76, and 78 are of the same diameter to provide support and alignment of the compressible retentate sheet.

The stacked cassettes 220 form a stack cassette array 222 which is retained between the plate 30 and end plate 60, as shown, with mechanical fastener means 85 being provided on the respective threaded rods to provide the necessary compressive action on the cassette array 222. The upper end plate features a permeate outlet conduit 52A and 52B, and a corresponding permeate egress conduit is provided on the opposite side at the bottom of plate 30, 62A and 62B. At the upper left-hand corner portion of mounting plate 30 is provided a retentate discharge conduit 8, and at the lower fight-hand of the filter is provided a feed material inlet conduit 44, as shown.

Inlet conduit 44 may be joined to a suitable source of material to be separated, which then can be provided under suitable temperature, pressure, and flow rate conditions to the filter 200 for separation therein into retentate, discharged in conduit 8, and permeate, discharged in conduit 52A and 52B (as well as the corresponding filtrate or permeate conduits 62A and 62B at the opposite lower portion of the filter).

Figure 6:
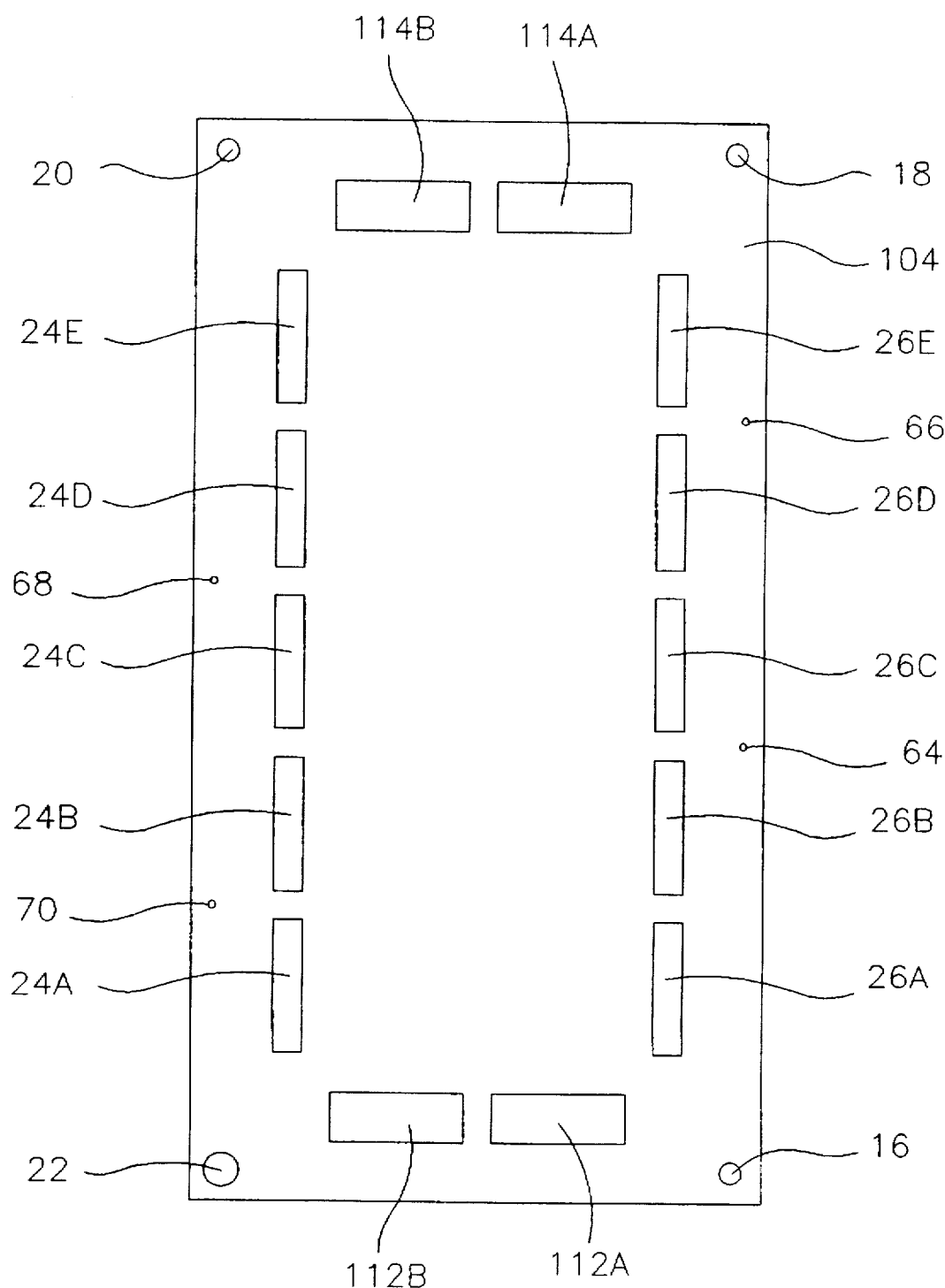
FIG. 6 is a plan view of a filter sheet of a type which may be usefully employed in the cassette of FIG. 2.

FIG. 6 is a plan view of a filter sheet of a type which may be usefully employed in the cassette of FIG. 2, and wherein all parts and elements are correspondingly numbered to FIG. 2.

Figure 7:
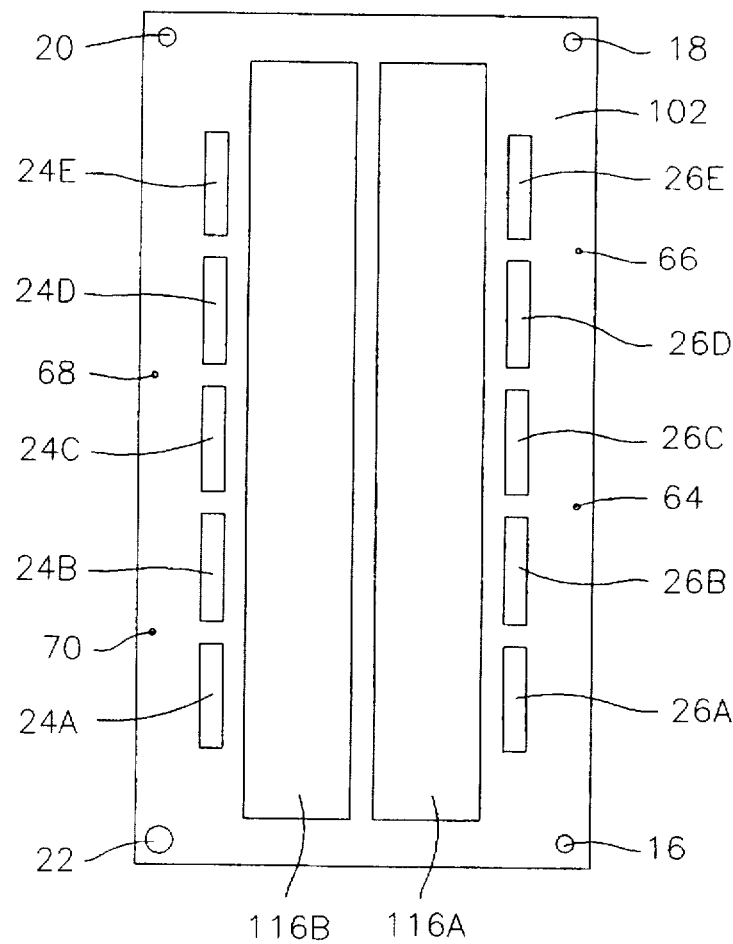
FIG. 7 is a plan view of a retentate sheet of a type which may be usefully employed in the cassette of FIG. 2.

FIG. 7 is a plan view of a retentate sheet of a type which may be usefully employed in the cassette of FIG. 2, and wherein all parts and elements are correspondingly numbered to FIG. 2.

Figure 7A:
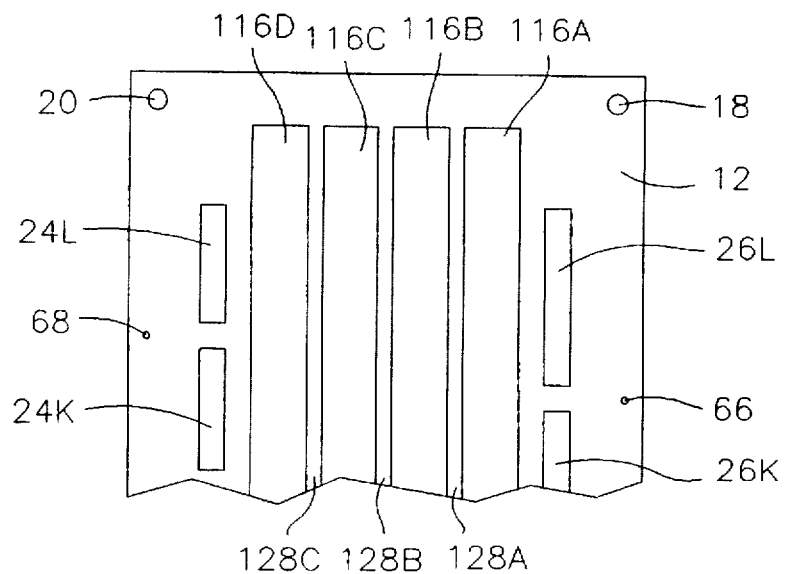
FIG. 7A is a top plan view of a portion of a retentate sheet according to another embodiment of the invention, featuring four quadrilateral-shaped basins.

FIG. 7A is a top plan view of a portion of a retentate sheet according to another embodiment of the invention, featuring four quadrilateral-shaped basins 116 A, B, C, and D, and featuring additional permeate channels 24 F–L and 26 F–L, beyond the corresponding two basin structure of FIG. 7, but wherein all other elements of FIG. 7A are numbered correspondingly to FIG. 7.

Figure 8:
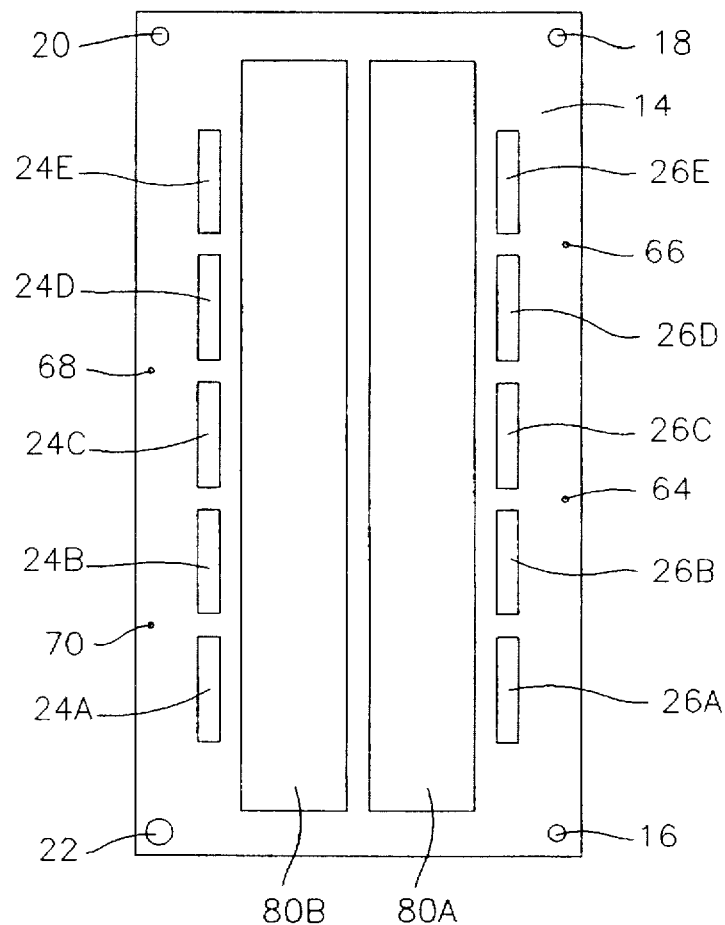
FIG. 8 is a plan view of a compressible end gasket of a type which may be usefully employed in the cassette of FIG. 2.

FIG. 8 is a plan view of a compressible end gasket of a type which may be usefully employed in the cassette of FIG. 2, featuring longitudinal retentate channels 80 A and B separated by rib 90, and wherein the permeate openings and rod mounting openings are numbered correspondingly to FIG. 2.

Figure 8A:
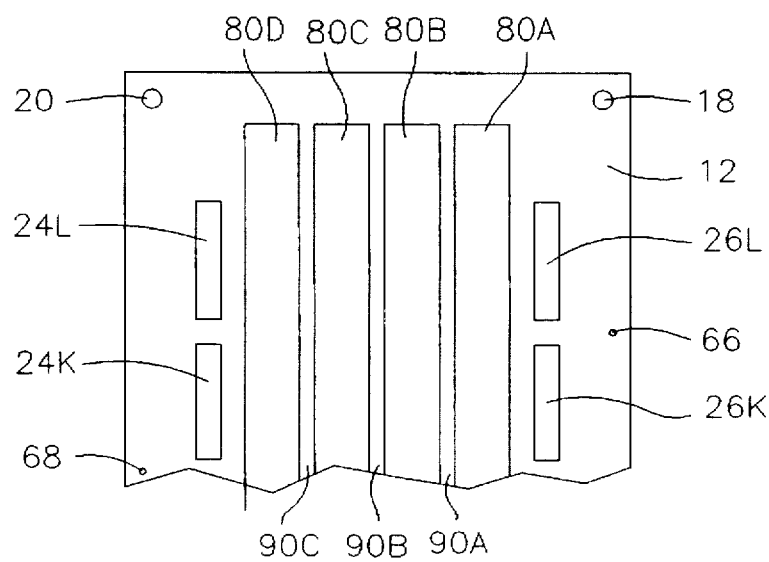
FIG. 8A is a plan view of a compressible end gasket according to another embodiment of the invention, featuring four quadrilateral-shaped basins.

FIG. 8A is a plan view of a compressible end gasket according to another embodiment of the invention, featuring four quadrilateral-shaped basins 80 A–D, separated by longitudinally extending, transversely spaced-apart ribs 90 A–C, and wherein the permeate openings and rod mounting openings are numbered correspondingly to FIG. 8 and FIG. 2.

Figure 9:
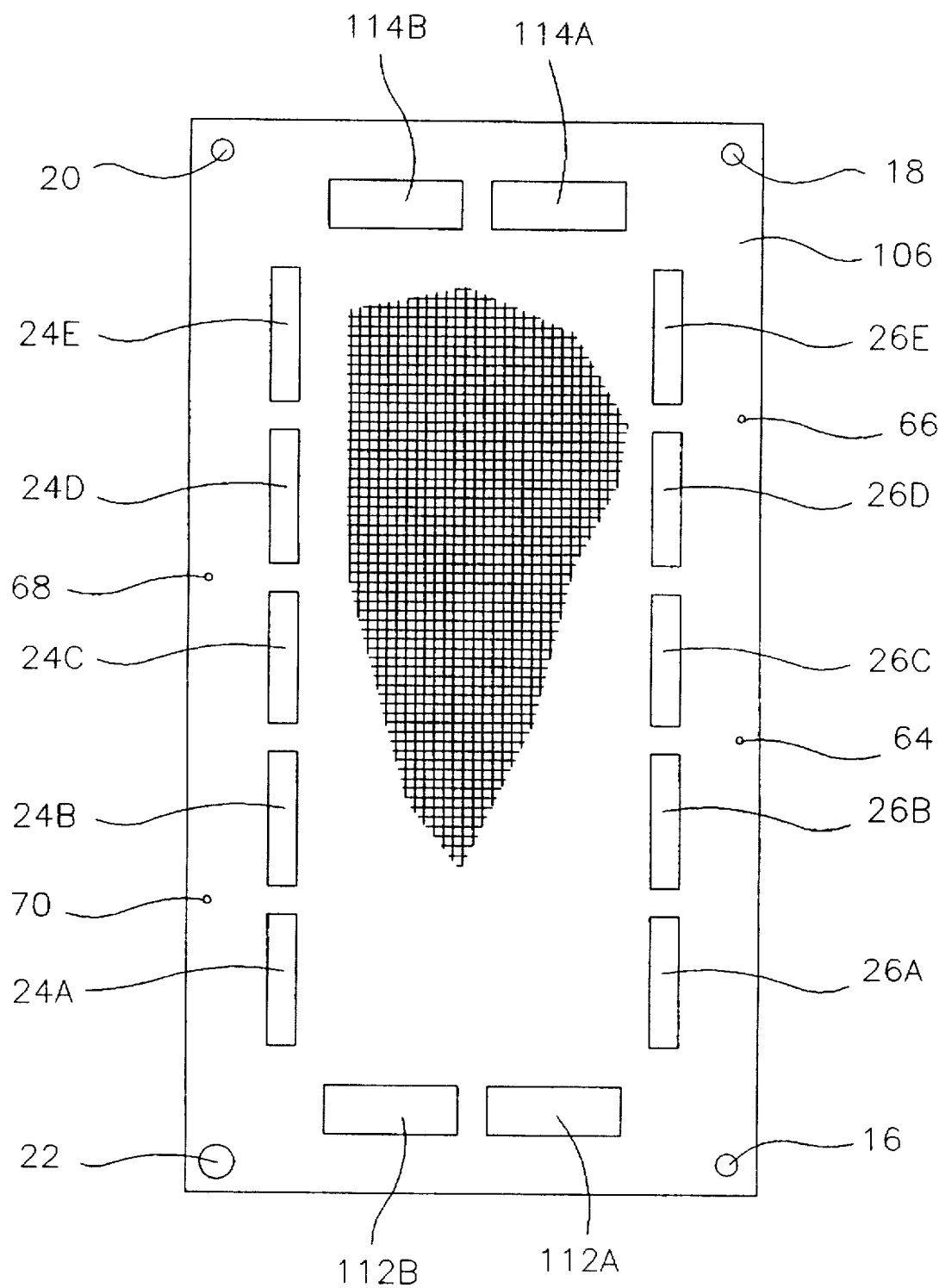
FIG. 9 is a plan view of a formaminous permeate sheet of a type which may be usefully employed in the cassette of FIG. 2.

FIG. 9 is a plan view of a formaminous permeate sheet of a type which may be usefully employed in the cassette of FIG. 2, and which is numbered correspondingly to FIG. 2.

Figure 10:
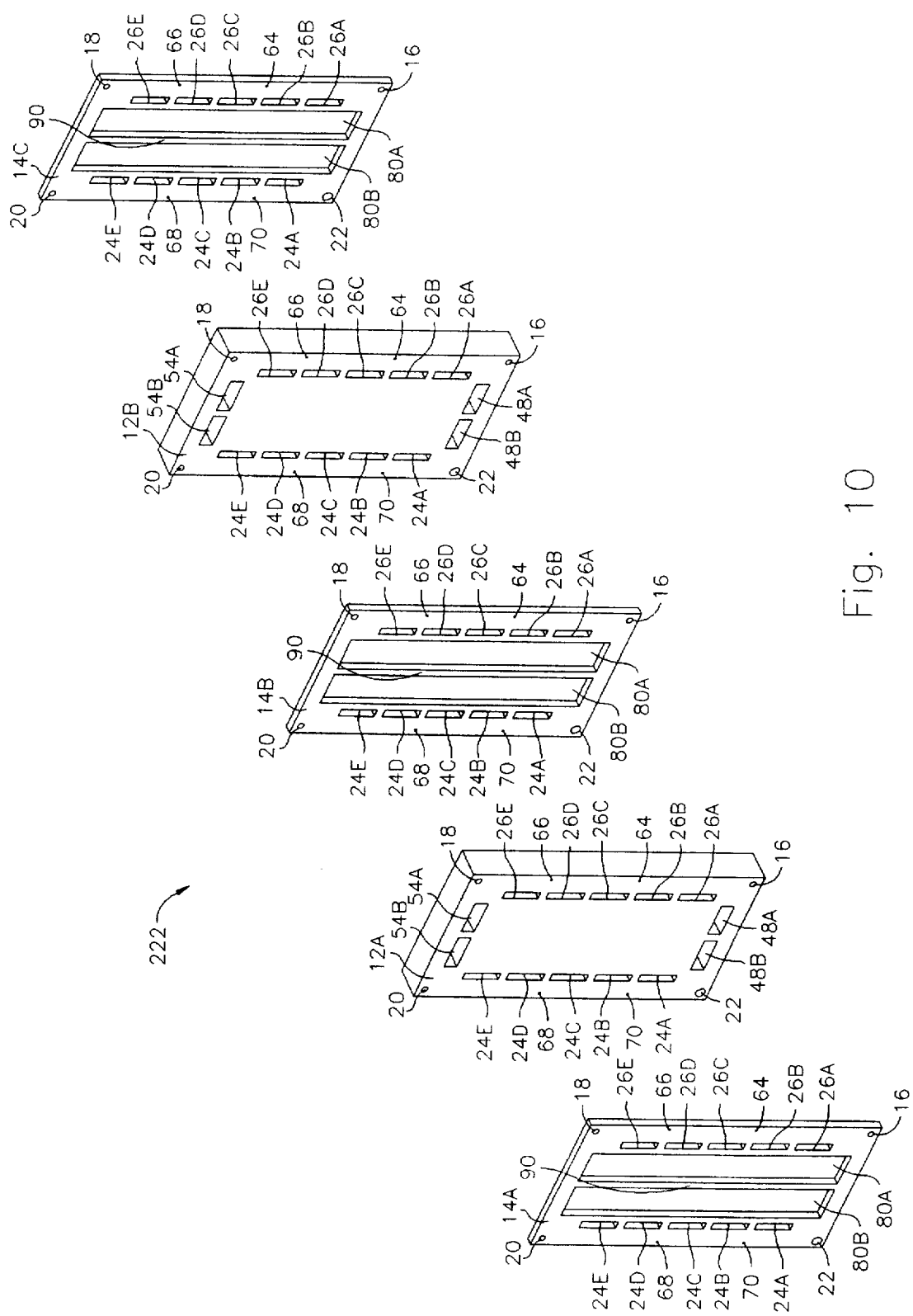
FIG. 10 is a perspective view of a filter comprising a multiplicity of cassettes and compressible end gaskets of the type shown in FIGS. 1 and 2.

FIG. 10 is a perspective exploded view of a filter 222 comprising a multiplicity of cassettes and compressible end gaskets of the type shown in FIGS. 1 and 2, and wherein corresponding parts and elements are numbered correspondingly to FIGS. 1 and 2.

Figure 11:
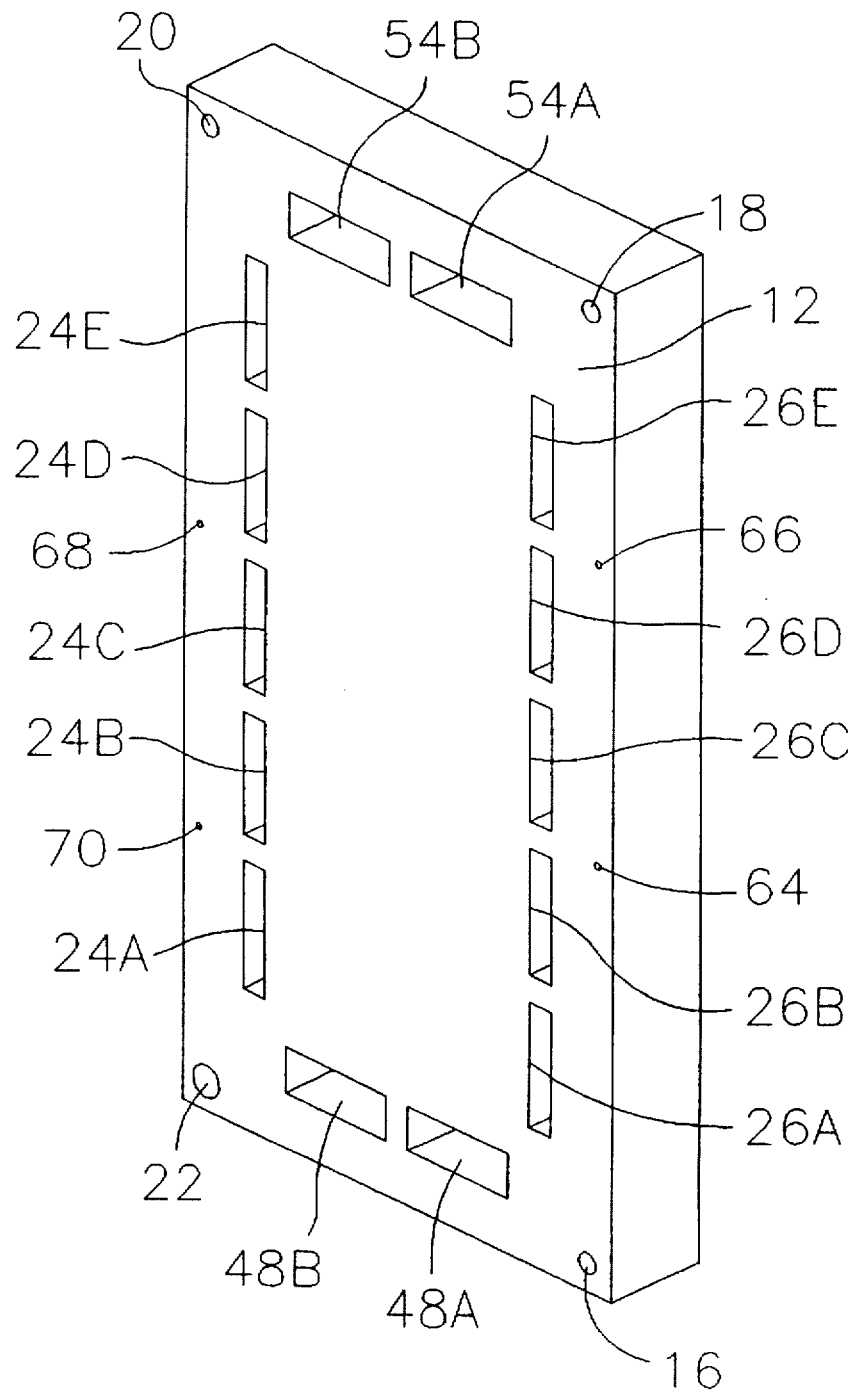
FIG. 11 is a top plan view of a filtration cassette according to one embodiment of the invention.

FIG. 11 is a perspective view of a filtration cassette according to one embodiment of the invention, wherein the parts and elements are numbered correspondingly to FIG. 2.

Figure 12:
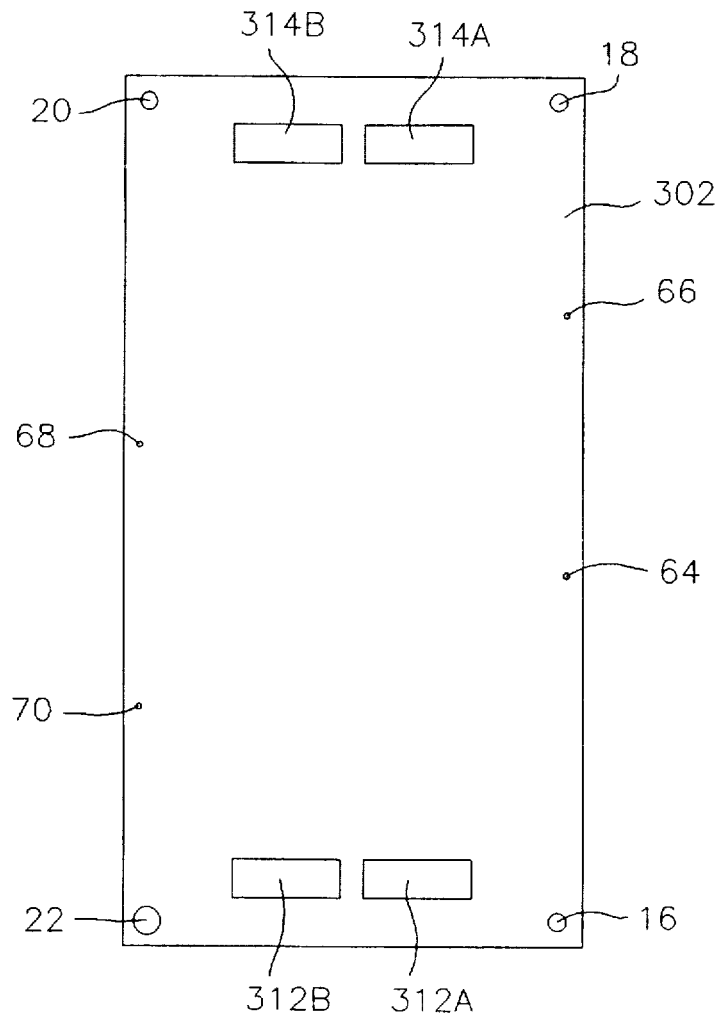
FIG. 12 is a top plan view of a portion of a cassette, composed of sheet members P/F/P featuring two quadrilateral-shaped basins after the first die cut.

FIG. 12 is a top plan view of a portion of a cassette 302, composed of sheet members P/F/P featuring two quadrilateral-shaped basins 314 A, B at one end portion of the multilaminate stack, and two quadrilateral-shaped basins 312 A, B at the other end portion of the multilaminate stack, after the first die cut.

Figure 12A:
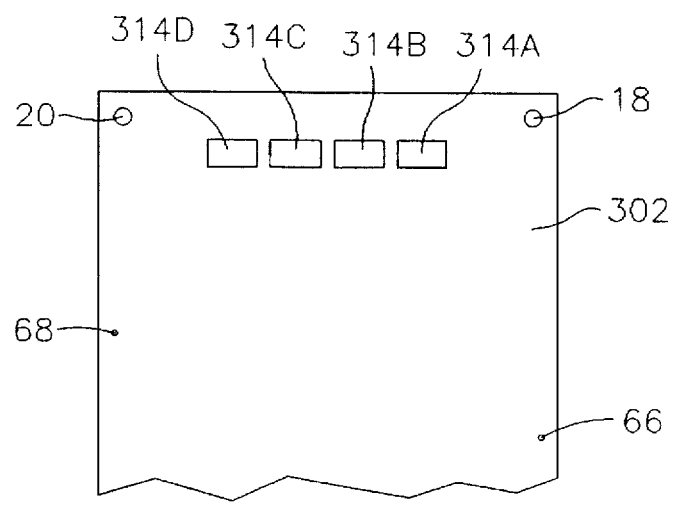
FIG. 12A is a top plan view of a portion of a filtration cassette, composed of sheet members P/F/P according to another embodiment of the invention, featuring four quadrilateral-shaped basins after the first die cut.

FIG. 12A is a top plan view of a portion of a filtration cassette, composed of sheet members P/F/P according to another embodiment of the invention, featuring four quadrilateral-shaped basins 314 A–D, after the first die cut.

Figure 13:
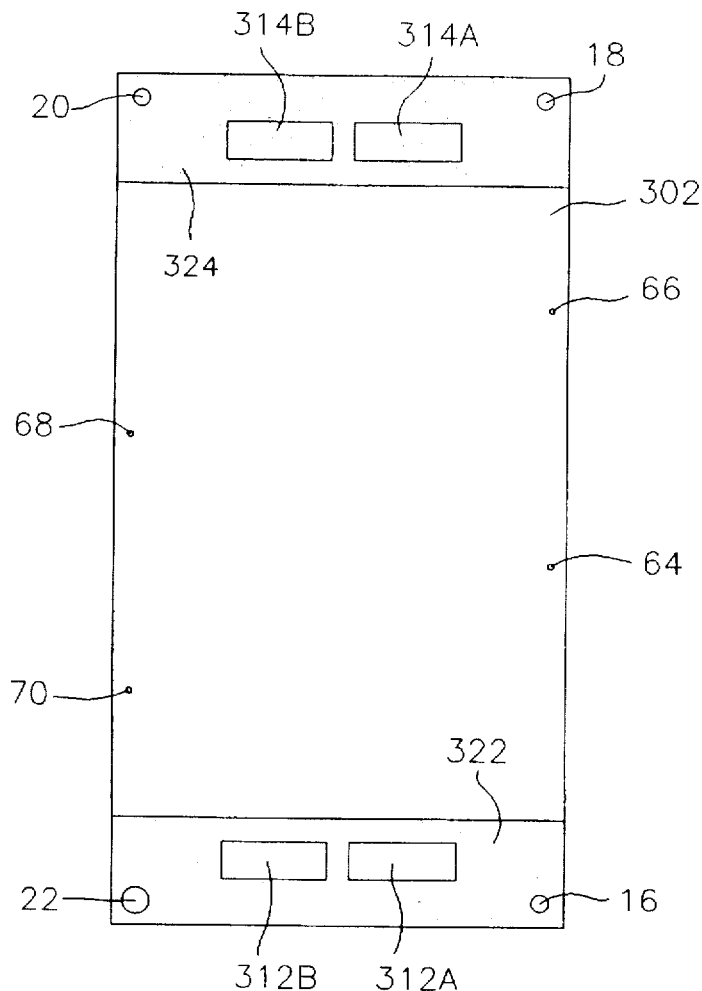
FIG. 13 is a top plan view of a portion of a cassette, composed of sheet members P/F/P after RF welding the encapsulating material, and featuring two quadrilateral-shaped basins.

FIG. 13 is a top plan view of a portion of the cassette of FIG. 12, numbered correspondingly thereto, and composed of sheet members P/F/P after RF welding the encapsulating material 324.

Figure 13A:
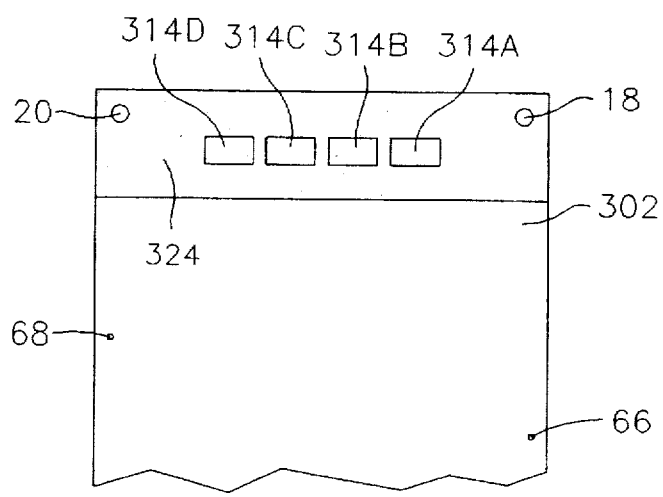
FIG. 13A is a top plan view of a portion of a filtration cassette, composed of sheet members P/F/P after RF welding the encapsulating material according to another embodiment of the invention, and featuring four quadrilateral-shaped basins.

FIG. 13A is a top plan view of a portion of the filtration cassette of FIG. 12A, numbered correspondingly thereto, and composed of sheet members P/F/P after RF welding the encapsulating material 324.

Figure 14:
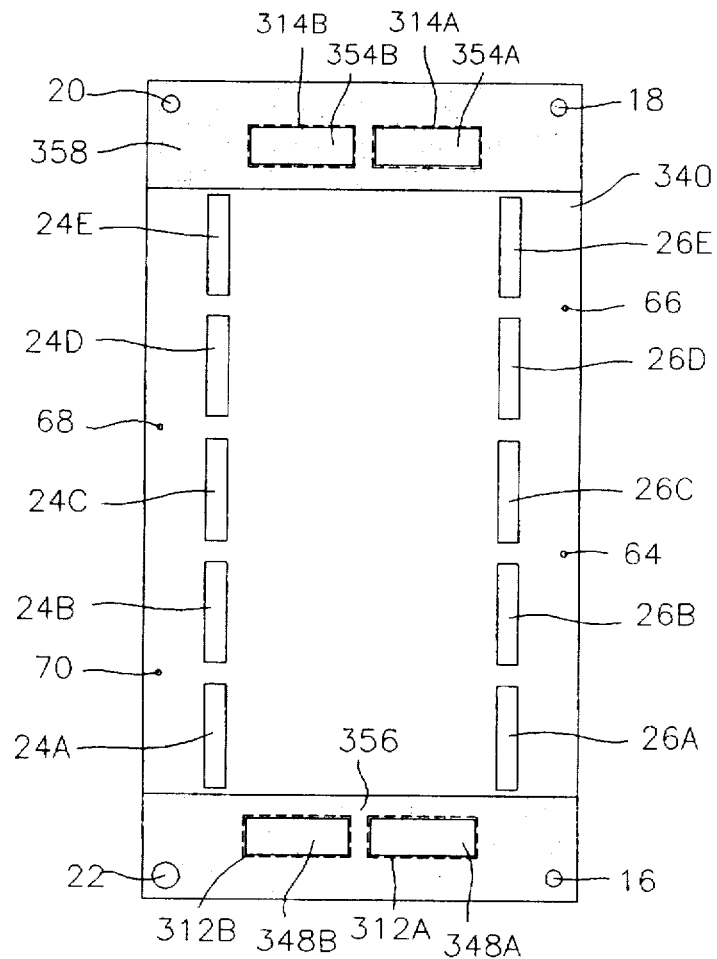
FIG. 14 is a top plan view of a portion of a cassette, composed of sheet members P/F/P after RF welding the encapsulating material, and featuring two quadrilateral-shaped basins after the second die cut.

FIG. 14 is a top plan view of the cassette of FIGS. 12 and 13, numbered correspondingly thereto, and composed of sheet members P/F/P after RF welding the encapsulating material, and featuring two quadrilateral-shaped basins after the second die cut.

Figure 14A:
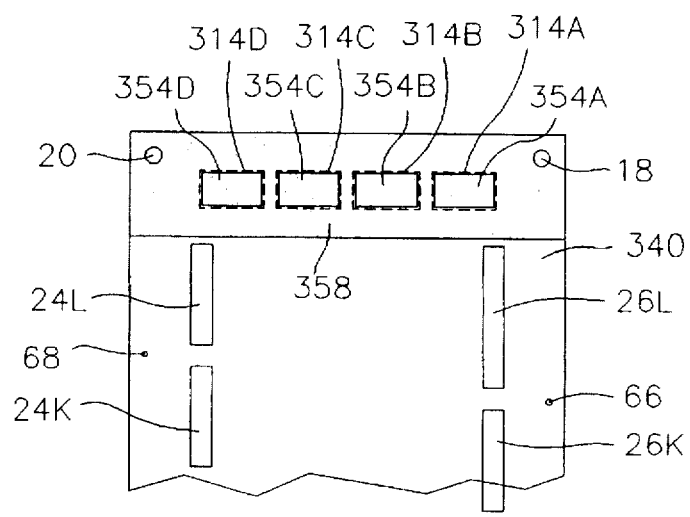
FIG. 14A is a top plan view of a portion of a filtration cassette, composed of sheet members P/F/P after RF welding the encapsulating material according to another embodiment of the invention, featuring four quadrilateral-shaped basins after the second die cut.

FIG. 14A is a top plan view of the filtration cassette of FIGS. 12A and 13A, numbered correspondingly thereto, and composed of sheet members P/F/P after RF welding the encapsulating material, and featuring four quadrilateral-shaped basins after the second die cut.

It will be apparent from the foregoing that the respective sections of stacked cassettes may be variously joined in fluid flow communication with one another, in parrallel or in series, to form stacked filter "trains" whose constituent sections may be employed to carry out a number of unit operations on an influent or feed material, such as concentrating (dewatering), washing, dialyzing, desalting, etc.

For example, a stacked filter train of series-connected sections may be employed in a culturing system of the type disclosed and claimed in my copending patent applications U.S. Ser. No. 06/936,486 filed Nov. 26, 1986, and U.S. Ser. No. 07/207,655 filed Jun. 21, 1988, the disclosures of which hereby are incorporated by reference, in applications such as the production in vitro of human immunodeficiency virus (HIV) on cellular or synthetic substrates. In such HIV production application, a first stacked cassette section could be employed to concentrate HIV, a second section could be utilized to add media to or withdraw media from the system, all without withdrawing any virus, such as may otherwise present a risk of immunosuppressive infection. Thus, a closed system virus culturing arrangement is provided, which is highly advantageous not only for the production of HIV but also the culturing or other processing of pathogenic as well as non-pathogenic bacterial, viral, anti yeast species.

While the invention has been described with reference to specific illustrative embodiments, it will be apparent that there are other variations, modifications, and embodiments possible within the broad scope of the invention, and that all such variations, modifications, and embodiments are to be regarded as being within the spirit and scope of the invention.

What is claimed is:

1. A filtration cassette comprising a multilaminate array of sheet members of generally rectangular and generally planar shape with main top and bottom surfaces, wherein the sheet members include in sequence in said array a first retentate sheet, a first filter sheet, a permeate sheet, a second filter sheet, and a second retentate sheet, wherein each of the sheet members in said array has at least one inlet basin opening at one end thereof, and at least one outlet basin opening at an opposite end thereof, with permeate passage openings at longitudinal side margin portions of the sheet members;

each of the first and second retentate sheets having at least one channel opening therein, wherein each channel opening extends longitudinally between the inlet and outlet basin openings of the sheets in the array and is open through the entire thickness of the retentate sheet, and with each of the first and second retentate sheets being bonded to an adjacent filter sheet about peripheral end and side portions thereof, with their basin openings and permeate passage openings in register with one another and the filtrate passage openings of each of the retentate sheets being circumscribingly compression bonded to the adjacent filter sheet, and with a central portion of each of the retentate sheets and adjacent filter sheets being unbonded to permit permeate contacting the retentate sheet to flow through the filter sheet to the permeate sheet; and each of the filter sheets being secured at its peripheral portions on a face thereof opposite the retentate sheet, to the permeate sheet.

2. A filtration cassette according to claim 1, wherein the inlet and outlet basin openings define distribution basins, each of which comprises two quadrilateral shaped sub-basins, and wherein each sub-basin comprises:

side edges intersecting at a first corner of the sub-basin defining a first included angle w therebetween of 90 degrees;

a second corner diagonally opposite said first corner, and the side edges intersecting at such second corner defining a second included angle x therebetween of 90 degrees;

a third corner transversely adjacent the first corner and longitudinally adjacent the second corner, with the side edges intersecting at the third corner defining a third included angle y therebetween of 90 degrees;

a fourth corner longitudinally adjacent the first corner and transversely adjacent the third corner, with the sides edges intersecting at the fourth corner defining a fourth angle z therebetween of 90 degrees.

3. A filtration cassette according to claim 1, wherein the inlet and outlet basin openings define distribution basins, each of which comprises four quadrilateral shaped sub-basins, and wherein each sub-basin comprises:

side edges intersecting at a first corner of the sub-basin defining a first included angle w therebetween of 90 degrees;

a second corner diagonally opposite said first corner, and the side edges intersecting at such second corner defining a second included angle x therebetween of 90 degrees;

a third corner transversely adjacent the first corner and longitudinally adjacent the second corner, with the side edges intersecting at the third corner defining a third included angle y therebetween of 90 degrees; and a fourth corner longitudinally adjacent the first corner and transversely adjacent the third corner, with the sides edges intersecting at the fourth corner defining a fourth angle z therebetween of 90 degrees.

4. A filtration cassette according to claim 1, wherein the permeate passage openings at each longitudinal side margin portion of each said sheet are longitudinally aligned with one another.

5. A filtration cassette according to claim 1, wherein each of the permeate and retentate sheets is foraminous and has a mesh size of from about 80 to about 300.

6. A filtration cassette according to claim 1, wherein each of the permeate and retentate sheets comprises a woven polymeric mesh.

7. A filtration cassette according to claim 6, wherein the woven polymeric mesh comprises a material selected from the group consisting of polyester, polypropylene, nylon, fluorocarbon polymers, polyethylene, and polysulfone.

8. A filtration cassette according to claim 1, wherein each of the retentate sheets have a thickness between 0.125 mm and 6.0 mm.

9. A filtration cassette according to claim 1, wherein each of retentate sheets is formed of a material selected from the group consisting of polysulfone, polyether sulfone, polyetherimide, polycarbonate, silicone, urethane.

10. A filtration cassette according to claim 1, wherein the filter sheets comprise a material selected from the group consisting of cellulose, polyphenylene oxide, polysulfone, cellulose nitrate, cellulose acetate, polyether amide, polyphenylene oxide/polysulfone blends, mixed esters of cellulose, regenerated cellulose, nylon, polyvinylidene fluoride, and polyethersulfone.

11. A filtration cassette according to claim 1, wherein the inlet and outlet basin openings are encapsulated with a reinforcing material.

12. A filtration cassette according to claim 11, wherein the reinforcing material is selected from the group consisting of urethane, silicone, ethylvinyl acetate, and EPDM.

13. A filtration cassette according to claim 11, wherein the reinforcing material is radio frequency (RF) welded.

14. A filtration cassette according to claim 11, wherein the reinforcing material is heat bonded.

15. A filtration cassette according to claim 1, wherein the array of sheet members comprises a non-compressible retentate sheet including a series of transversely spaced-apart, longitudinally extending ribs, each extending outwardly from the plane of the sheet to an outer extremity, with filter sheets bonded to the non-compressible retentate sheet at rib outer extremities on respective main faces of said non-compressible retentate sheet.

16. A filtration cassette according to claim 15, wherein the longitudinally extending ribs are formed of an adhesive bonding material.

17. A filtration cassette according to claim 16, wherein the adhesive bonding material comprises a material selected from the group consisting of urethane, epoxy, cyanoacrylate, and silicone adhesives.

18. A filtration cassette according to claim 1, wherein the sheets in the cassette are bonded to one another with an adhesive bonding medium comprising a material selected from the group consisting of urethane, epoxy, cyanoacrylate, and silicone adhesives.

19. A filtration cassette according to claim 1, further comprising a feed material inlet port communicating with said at least one inlet basin opening, and a retentate outlet port communicating with said at least one outlet basin opening, with one of said inlet and outlet ports being on one of said main top and bottom surfaces, and the other of said inlet and outlet ports being on the other of said main top and bottom surfaces.

20. A filtration cassette according to claim 1, further comprising a feed material inlet port communicating with said at least one inlet basin opening, and a retentate outlet port communicating with said at least one outlet basin opening, wherein the inlet and outlet ports are diagonally opposite one another on said cassette.

21. A stacked cassette filter including a stacked assembly of filtration cassettes each comprising a multilaminate array of sheet members of generally rectangular and generally planar shape with main top and bottom surfaces, wherein each filtration cassette comprises a multilaminate array of sheet members of generally rectangular and generally planar shape with main top and bottom surfaces, wherein the sheet members include in sequence in said array a first retentate sheet, a first filter sheet, a permeate sheet, a second filter sheet, and a second retentate sheet, wherein each of the sheet members in said array has at least one inlet basin opening at one end thereof, and at least one outlet basin opening at an opposite end thereof, with permeate passage openings at longitudinal side margin portions of the sheet members;

each of the first and second retentate sheets having at least one channel opening therein, wherein each channel opening extends longitudinally between the inlet and outlet basin openings of the sheets in the array and is open through the entire thickness of the retentate sheet, and with each of the first and second retentate sheets being bonded to an adjacent filter sheet about peripheral end and side portions thereof, with their basin openings and permeate passage openings in register with one another and the filtrate passage openings of each of the retentate sheets being circumscribingly compression bonded to the adjacent filter sheet, and with a central portion of each of the retentate sheets and adjacent filter sheets being unbonded to permit permeate contacting the retentate sheet to flow through the filter sheet to the permeate sheet; and each of the filter sheets being secured at its peripheral portions on a face thereof opposite the retentate sheet, to the permeate sheet.

22. A stacked cassette filter according to claim 21, wherein the stacked assembly comprises a number X of filter sheets, 0.5X–1 retentate sheets, and 0.5X permeate sheets, and two compressible retentate sheets.

23. A filtration cassette comprising a sequence of stacked sheet members including outermost retentate sheets, wherein said stacked sheet members comprise a compressible retentate sheet designated "CR", a first filter sheet designated "F", a foraminous permeate sheet designated "P", a second filter sheet designated "F", and a second compressible retentate sheet designated "CR", arranged in the sequence of sheet members, CR/F/P/F/CR, and wherein the stacked sheet members includes multiple discrete basin openings at each of its end extremities defining inlet basin openings at one end of the stacked sheet members and outlet basin openings at the other end of the stacked sheet members, each of said multiple discrete basin openings extending through the stacked sheet members, with multiple discrete permeate passage openings along the longitudinal side margins of the stacked sheet members extending therethrough, and with the retentate sheets having open channels therein for passage therethrough of fluid to be separated into retentate and permeate, and wherein the sheets in the cassette are peripherally bonded to form a peripherally leak-tight bonded assembly of stacked sheet members.

24. A filtration cassette according to claim 23, wherein the stacked sheet members comprise first compressible retentate sheet "CR", filter sheets "F", foraminous permeate sheets P, non-compressible retentate sheets "R" and second compressible retentate sheet "CR" in a sheet sequence CR/F/P/F/R/F/P/F/R/F/P/F/CR.

25. A filtration cassette according to claim 23, wherein the stacked sheet members comprise first compressible retentate sheet "CR", filter sheets "F", foraminous permeate sheets P, non-compressible retentate sheets "R" and second compressible retentate sheet "CR" in a sheet sequence wherein X is the number of filter sheets F, the quantity 0.5X–1 is the number of non-compressible retentate sheets R, and the quantity 0.5X is the number of foraminous permeate sheets P, and with two compressible retentate sheets being utilized to seal the top and bottom extremeties of the sequence.

26. A filtration cassette according to claim 23, wherein the stacked sheet members comprise first compressible retentate sheet "CR", filter sheets "F", foraminous permeate sheets P, non-compressible retentate sheets "R" and second compressible retentate sheet "CR" in a sheet sequence comprising at least one base sequence F/P/F, with each of outermost compressible retentate sheets in the sequence being compression-sealed at outer faces thereof to an end plate accommodating removal of permeate from permeate passage openings of the cassette.

27. A filtration cassette according to claim 23, wherein the basin openings in the cassette are encapsulated at peripheries thereof with a reinforcing material.

28. A filtration cassette according to claim 23, further comprising a feed material inlet port in communication with said inlet basin openings and a retentate outlet port in communication with said outlet basin openings, wherein the inlet and outlet ports are on opposite sides of the stacked sheet members.

29. A filtration cassette according to claim 23, further comprising a feed material inlet port in communication with said inlet basin openings and a retentate outlet port in communication with said outlet basin openings, wherein the inlet and outlet ports are diagonally opposite one another in relation to the sequence of stacked sheet members.

* * * * *

UNITED STATES PATENT AND TRADEMARK OFFICE
CERTIFICATE OF CORRECTION

PATENT NO. : 5,593,580
DATED : January 14, 1997
INVENTOR(S) : Henry B. Kopf

It is certified that error appears in the above-indentified patent and that said Letters Patent is hereby corrected as shown below:

Column 19, Line 54     "fight-hand" should be -- right-hand --

Signed and Sealed this

Eighth Day of July, 1997

Attest:

BRUCE LEHMAN

*Attesting Officer*     *Commissioner of Patents and Trademarks*